United States Patent [19]

Uchida et al.

[11] Patent Number: 5,552,292
[45] Date of Patent: Sep. 3, 1996

[54] METHOD OF SCREENING FOR COLORECTAL CANCER

[75] Inventors: Kazuo Uchida, Hyogo-ken; Shinichi Mashiba, Kyoto-fu, both of Japan

[73] Assignee: Ikagaku Co., Ltd., Kyoto, Japan

[21] Appl. No.: 339,192

[22] Filed: Nov. 10, 1994

Related U.S. Application Data

[63] Continuation-in-part of Ser. No. 113,134, Aug. 30, 1993, abandoned.

[30] Foreign Application Priority Data

Jan. 18, 1993 [JP] Japan ............................. 5-5676
Jul. 8, 1993 [JP] Japan ........................... 5-194089
Jul. 5, 1994 [JP] Japan ........................... 6-177647

[51] Int. Cl.$^6$ .................. G01N 33/53; G01N 33/574
[52] U.S. Cl. ..................... 435/7.23; 435/7.4; 435/7.9; 435/7.92; 435/7.24; 436/63; 436/64; 436/813
[58] Field of Search ........................ 435/7.23, 7.4, 435/7.9, 7.92, 7.24; 436/63, 64, 813

[56] References Cited

U.S. PATENT DOCUMENTS

5,124,252  6/1992  Guerrant et al. ...................... 435/7.24

FOREIGN PATENT DOCUMENTS

WO92/16843  10/1992  WIPO .

OTHER PUBLICATIONS

Abbas, A. K., et al, Cellular and Molecular Immunology, W. G. Sauders Company, Philadelphia, p. 22, 1991.
Dunn, T. L., et al, Analytical Biochemistry, 150, 18–25 (1985).
Edwards, Ray, Immunoassay Introduction, 1985, William Heineman Medical books, Ltd., Japanese Version, p. 91 and translation of Table 6.2.
Harlow, E., et al, Antibodies, A Laboratory Manual, Cold Spring Harbor Laboratory, Cold Spring Harbor, N.Y., pp. 349, 580–581, 1988.
Harrison's Principles of Internal Medicine, 12th edition, vol. 2, Wilson, J. D., et al, editors, 1289–1293.
Isselbacher, K. J., et al, eds., Harrison's Principles of Internal Medicine, 9th edition, McGraw-Hill, New York, 1424–1435 (1980).
Isselbacher, K. J., et al, eds, Harrison's Principles of Internal Medicine, 9th edition, pp.1434–1436, McGraw-Hill, New York, 1980.
Merck Booklet 15689, PMN Elastase–Merck Immunoassay–undated.
Saville, J. S., et al, J. Clin. Invest., vol. 83, 865–875 (Mar. 1989).
Faymonville, M. E., et al, Journal of Thoracic and Cardiovascular Surgery 102: 309–317, 1991.
Gross, V., et al, Granulocyte Elastase in Plasma and Faeces as a Marker for Disease Activity in Patients with Inflammatory bowel Diseases, Gastroenterology 100 (5 pt. 2), A583, 1991.
Guerrant, R. L., et al, Journal of Clinical Microbiology, vol. 30, No. 5, 1238–1242 (May 1992).

*Primary Examiner*—Toni R. Scheiner

[57] ABSTRACT

The invention provides a new method for screening for colorectal cancer by measurement of the level of lactoferrin or myeloperoxidase in feces. Particularly, a screening test method for colorectal cancer by measurement of the level of lactoferrin or myeloperoxidase in feces by immunoassay and by measurement of the level of whole-sized lactoferrin by immunoassay utilizing monoclonal antibody.

9 Claims, 23 Drawing Sheets

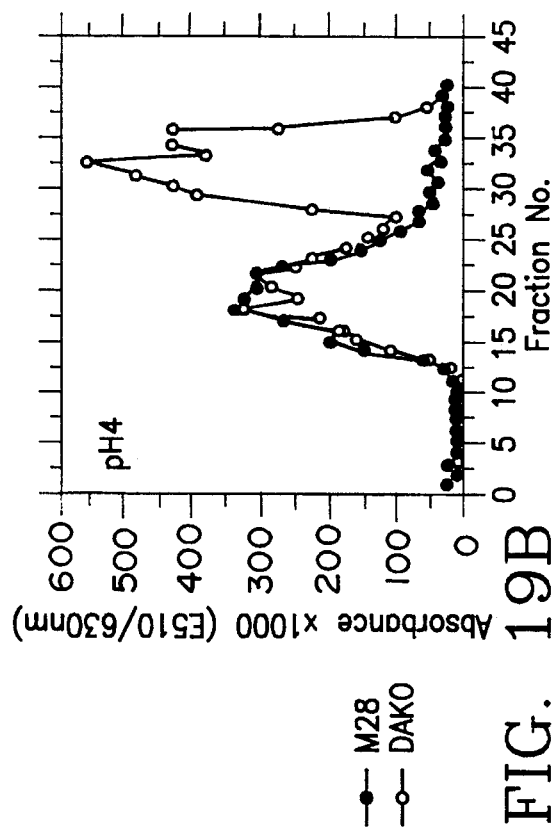
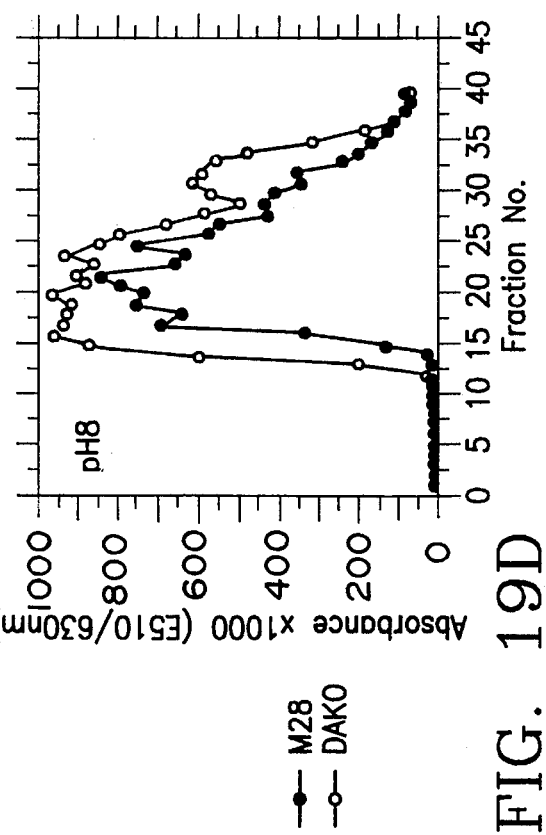
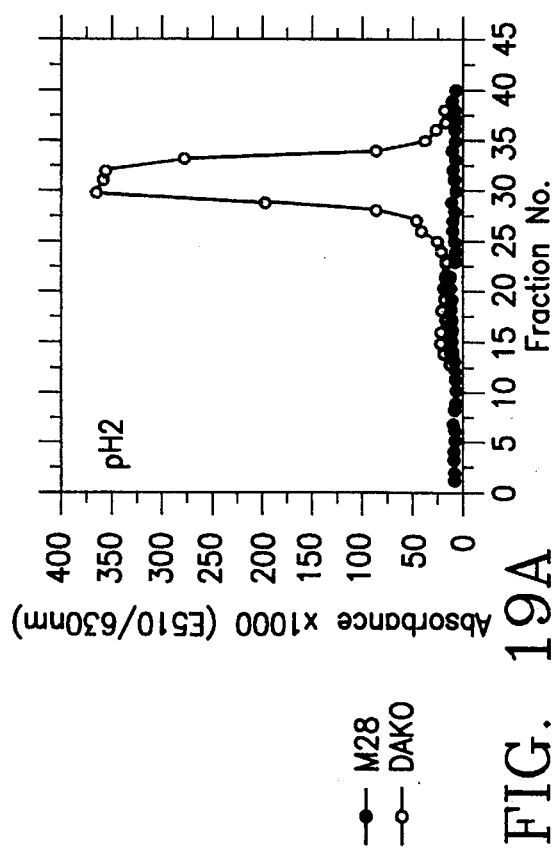
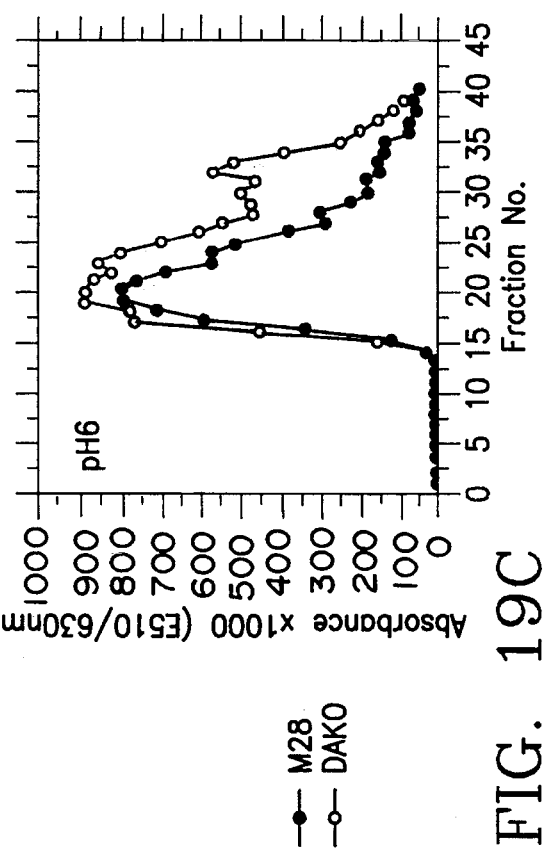

METHOD OF SCREENING FOR COLORECTAL CANCER

This is a continuation in-part application of U.S. patent application Ser. No. 08/113,134 filed on Aug. 30, 1993, now abandoned.

BACKGROUND OF THE INVENTION

1. Field of the Invention

The present invention relates to a method for diagnosis of gastrointestinal tract disorders by measurement of the level of lactoferrin, myeloperoxidase or polymorphonuclear leucocyte elastase in feces. Particularly, a screening test method for colorectal cancer by measurement of the level of lactoferrin or myeloperoxidase in feces by immunoassay and by measurement of the level of whole-sized lactoferrin by immunoassay utilizing monoclonal antibody. 2. Description of the Prior Art In various kinds of gastrointestinal tract diseases such as inflammatory gastrointestinal disorders and gastrointestinal cancer, intestinal chronic bleeding is observed in inflammation neoplasia at the mucous membrane, or protein leaking in gastrointestinal tract is observed due to permeability disorder of capillary blood vessel or pressure raise of lymphoduct.

In order to diagnose the gastrointestinal tract diseases, the fecal occult blood test method has most been used for screening of gastrointestinal tract diseases with bleeding, especially for mass screening of colorectal cancer.

Among the fecal occult blood test, the guaiac method is the most widely used and the method utilizes the peroxidase activity of the heme in hemoglobin, hence not only human hemoglobin in feces, but also hemoglobin from animal and fish meat or special vegetable is detected by this method. Since human hemoglobin is not detected specifically by the Guaiac method, subjects are required to follow a special diet in order to prevent the occurrence of false positive results. Moreover, it has been difficult to increase the sensitivity of this method.

In recent years, as the fecal occult blood test, immunological methods using an anti-human hemoglobin antibody e.g. enzyme immunoassay or latex agglutination has been developed. These methods have high specificity and high sensitivity for human hemoglobin and do not require a special diet. However, the stability of hemoglobin in feces is low, which sometimes induces false negative results. Other problems in the diagnosis of gastrointestinal tract disease by fecal occult blood test are false positive readings resulting from the admixture of blood from sources other than the gastrointestinal tract, for example, blood from damaged blood vessels of the anus and physiological loss of blood.

Now it has been found that an amount of a neutrophil leucocyte releasing substance in feces, particularly, lactoferrin, myeloperoxidase or polymorphonuclear leucocyte elastase, have a good relation to the diagnosis of inflammatory gastrointestinal disorders, colon polyp or colorectal cancer.

A method for diagnosis of inflammatory diarrhea by latex agglutination assay or enzyme-linked immunosorbent assay using a fecal leucocyte releasing substance, specifically lactoferrin as a marker, was disclosed in U.S. Pat. No. 5,124,252, which is however directed to distinguish whether it is the invasive and inflammatory diarrhea usually caused by bacteria such as Shigella, Salmonella or Clostridium. The above invention does not relate to diagnosis for inflammatory gastrointestinal disorders, colon polyp and colorectal cancer which are not caused by invasion or infection.

As the result of an extensive study to overcome the above drawbacks and problems as seen in the known method, now we have developed a new method for diagnosis of inflammatory gastrointestinal tract disorders, colon polyp or colorectal cancer.

SUMMARY OF THE INVENTION

There is now developed a new method for diagnosis of inflammatory gastrointestinal disorders, colon polyp or colorectal cancer, in which, as a detection marker, neutrophil leucocyte releasing substances, i.e. lactoferrin, myeloperoxidase or polymorphonuclear leucocyte elastase is used, an amount thereof determined by a per se conventional immunoassay technique that employs an antibody against the human neutrophil leucocyte releasing substance and compared with a reference value as previously established on healthy persons and a kit therefor.

The substances released by neutrophil leukocytes are: various hydrolytic enzymes and basic proteins with low molecular weight contained in granules of neutrophil leukocytes, and active oxygen species produced by activated neutrophil leukocytes. Specifically, there are exemplified lactoferrin, polymorphonuclear leucocyte elastase, myeloperoxidase, lysozyme and capthesin-G.

As the result of the following studies, lactoferrin, myeloperoxidase and polymorphonuclear leucocyte elastase were selected as the object for the determination for the diagnosis of gastrointestinal disorders, colon polyp or colorectal cancer.

The efficiency of neutrophil leucocyte releasing substances in diagnosis of gastrointestinal disorders were evaluated, and the results as follows: re sensitivity for ulcerative colitis, lactoferrin 91.4%, myeloperoxidase 75.9%, polymorphonuclear leucocyte elastase 86.2% and lysozyme 87.9%; re sensitivity for Crohn's disease, 98.1%, 44.2%, 84.5% and 86.5%, respectively. The specificity was the same, 97.1%, for all markers (data not shown).

Also the lactoferrin assay was compared with immunochemical fecal occult blood test in inflammatory gastrointestinal disorders such as ulcerative colitis, crohn's disease and colorectal cancer (Table 1).

Table 1
Evaluation of the lactoferrin assay and immunochemical fecal occult blood test in inflammatory gastrointestinal disorders and colon cancer.

|  | Ulcerative colitis | | Crohn's disease | | Colon cancer | |
| --- | --- | --- | --- | --- | --- | --- |
|  | LF (%) | Hb (%) | LF (%) | Hb (%) | LF (%) | Hb (%) |
| Sensitivity | 91.4 | 79.3 | 98.1 | 63.5 | 100.0 | 92.3 |
| Specificity | 97.1 | 94.3 | 97.1 | 94.3 | 97.1 | 94.3 |

The results show that lactoferrin is preferred to hemoglobin as a detection marker for these diseases.

A neutrophil leucocyte releasing substance, for example, lactoferrin is contained in special (secondary) granules of neutrophil leukocytes, not in lymphocytes of monocytes. It is also contained in serum, saliva and breast milk; however, lactoferrin is considered to originate from leukocytes. Saliva contains 5–10 µg/ml of lactoferrin. However, since only a small amount of lactoferrin, 0.75±0.83 µg/g feces, was detected in feces of the control group, it is thought that most of the lactoferrin contained in saliva is digested and decomposed. Moreover, lactoferrin measurement is not affected by blood in feces unless the amount of blood present exceeds 25–50 ml per 100 g feces (Experiment 1). It is also unaffected by dairy products in the diet, because an anti-human-lactoferrin antibody does not cross-react with cow lactoferrin (Experiment 2, FIG. 1).

The stability of the neutrophil leucocyte releasing substances was studied and the result is as follows: lactoferrin was the most stable substance in feces; it lost only 10% of its activity when the feces were kept at room temperature (25° C.) for 4 days, myeloperoxidase and polymorphonuclear leucocyte elastase were lost 20% and 30% in the same conditions, respectively (Experiment 3, FIG. 2). The stability of lactoferrin was compared with that of hemoglobin at 25° C. in solid feces (Experiment 3, FIG. 3) and the results show that lactoferrin is preferred to hemoglobin as the detection marker.

In the clinical examination, lactoferrin measurements were compared with the results of the immuno fecal occult blood test. Both test results were positive in all of the patients with active ulcerative colitis. However, the lactoferrin, myeloperoxidase and leucocyte elastase were positive in 75%, 85% and 75% of the patients with inactive ulcerative colitis, respectively, whereas the immunochemical fecal occult blood test was positive in only 40% of patients. Moreover, the positive ratio of the lactoferrin myeloperoxidase and leucocyte elastase measurement were significantly higher than that of the immunochemical fecal occult blood test in patients with active or inactive Crohn's disease, in which plasma protein loss usually occurs rather than gastrointestinal tract bleeding. These findings are indicative of the superiority of lactoferrin myeloperoxidase and leucocyte elastase as the detection markers for inflammatory gastrointestinal disorders. There is also a tendency for the positive ratio of lactoferrin measurement to exceed that of the immunochemical fecal occult blood test in patients with colorectal cancer and colon polyp (Table 2).

established on healthy persons, and a kit for diagnosis of inflammatory gastrointestinal tract disorders or colorectal cancer from a fecal sample of a person to be diagnosed, which comprises (a) an antibody against a human neutrophil leukocytes releasing substance to be immobilized to a solid phase, (b) an enzyme-linked antibody against human neutrophil leukocytes releasing substance, i.e. lactoferrin, myeloperoxidase or polymorphonuclear leucocyte elastase and (c) a chromogen which is colored by enzyme The term "inflammatory gastrointestinal tract disorders" means gastrointestinal disorders such as active or inactive ulcerative colitis or active or inactive Crohn's diseases which is inflammatory and but not invasive or not infectious. The method of the invention can be also applied to colon polyp and colorectal cancer.

The term "immunoassay" includes conventional immunological techniques, for example, radioimmunoassay, immunoradiometric assay, enzyme-linked immunosorbent assay (ELISA), enzyme labelled immunometric assay, fluorescent labelled immunoassay, luminescent labelled immunoassay, immunoprecipitation assay or particle and agglutination immunoassay. See also Ray Edwards, Immunoassay, An introduction, 1985, William Heineman Medical Books LTD., and the content is hereby incorporated into the specification by reference.

"A reference value" is established on a group consisting of healthy persons who demonstrate no abnormality in the upper gastrointestinal tract, as confirmed by endoscopy, and no abnormality in the colon, as confirmed either by coloscopic examination or barium enema and/or apparently healthy persons. In order to obtain the reference value, an amount of neutrophil leucocyte releasing substance, i.e. lactoferrin, myeloperoxidase or polymorphonuclear leukocytes is determined by the method of the invention. The reference value for a neutrophil leukocytes releasing substance is defined as a mean value of control group+2SD (SD: standard deviation). It is noted that the reference value for the substance under consideration was present between the upper limit of the concentration of the substance μg/g feces

TABLE 2

Comparison of positive rate of lactoferrin, myeloperoxidase and polymorphonuclear leucocyte elastase with immunochemical occult blood test

| Diagnosis | No. tested | Lactoferrin | Myeloperoxidase | Polymorphonuclear leucocyte elastase | Occult blood |
|---|---|---|---|---|---|
| Control | 35 | 2.9% (1/35) | 2.9% (1/35) | 2.9% (1/35) | 5.7% (2/35) |
| Colon polyp | 16 | 43.8% (7/16) | 43.8% (7/16) | 31.3% (5/16) | 25.0% (4/16) |
| Colon cancer | 13 | 100.0% (13/13) | 100.0% (13/13) | 69.2% (9/13) | 92.3% (12/13) |
| Ulcerative colitis (active) | 38 | 100.0% (38/38) | 94.7% (36/38) | 97.4% (37/38) | 100.0% (38/38) |
| Ulcerative colitis (inactive) | 20 | 75.0% (15/20) | 85.0% (17/20) | 75.0% (15/20) | 40.0% (8/20) |
| Crohn's disease (active) | 36 | 100.0% (36/36) | 100.0% (36/36) | 97.2% (35/36) | 72.2% (26/36) |
| Crohn's disease (inactive) | 16 | 93.8% (15/16) | 68.8% (11/16) | 68.8% (11/16) | 43.8% (7/16) |

DETAILED DESCRIPTION OF THE INVENTION

The invention provides a method for diagnosis of inflammatory gastrointestinal tract disorders, colon polyp or colorectal cancer from a fecal sample of a person to be diagnosed and which comprises determining an amount of at least one of lactoferrin, myeloperoxidase and polymorphonuclear leucocyte elastase in the fecal sample by immunoassay and comparing said amount with a reference value as obtained from healthy persons and the lower limit of the concentration of the substance μg/g feces obtained from patients with inflammatory gastrointestinal disorders, colon polyp or colorectal cancer.

In case of colorectal cancer, the reference value, i.e. the cut-off value for lactoferrin is about 2.4 μg/g feces as shown in Example 2 under item 3.(5) and FIG. 7 as well as the reference value, i.e. the cut-off value for myeroperoxidase is about 4.2 μg/g feces as shown in Example3 under item 3.(5) and FIG. 8.

Antibodies against human neutrophil leucocyte releasing substances are commercially available.

As enzyme used in "enzyme-linked immunoassay" are exemplified peroxidase, β-galactosidase and alkaline phosphatase.

Summary of the method according to the present invention is given as follows.

The fecal sample obtained from a patient to be diagnosed was immediately cooled at 0° C. and well mixed. The sample is measured, mixed with TBS buffer and applied to immunoassay. For example, enzyme-linked immunoassay was conducted as follows: (1) An antibody against a human neutrophil leucocyte releasing substance is added to each well of a 96-well polystyrene microplate and immobilized thereto. (2) The same kind of an antibody as used in (1) is labelled with an enzyme by an conventional method, e.g. by the periodic acid Schiff stain method. (3) BSA and TBS are separately injected into the well to which the antibody has been previously immobilized in (1), and to which a solution of the fecal sample is added. The mixture is allowed to stand at 37° C. (first reaction) and then the well is sufficiently washed with deionized water containing Tween 20. (4) A BSA Tris-saline buffer solution of the enzyme-linked antibody prepared in (2) is added to the well, allowed to react at 37° C. (second reaction) and the well is fully washed. (5) A substrate buffer is added to the well and this is allowed to react at 37° C. Then coloring reagent is added to the well to produce a color reaction. The color of the well was assessed by determining absorbance at an optimum wave length with a microplate photometer. The concentration in the fecal sample was obtained from a quantification curve, and the amount is compared with the reference value of the substance under consideration.

Therefore, a kit according to the invention usually comprises an antibody against a human neutrophil leucocyte releasing substance to be immobilized, an enzyme-linked antibody of the same kind antibody as immobilized, a reagent containing a substrate and a coloring reagent.

Now we have also found that in colorectal cancer, especially in its early stage when inflammatory lesions are not observed in the diseased part, whole-sized lactoferrin (refer to below) can be nevertheless detected in the fecal samples from patients with colorectal cancer in an amount of more than a cut-off value in fecal samples from healthy persons, and whole-sized lactoferrin in feces was also a good marker for screening of colorectal cancer.

Therefore, the present invention also provides a screening test method for colorectal cancer carried out on a fecal sample of a person suspected of suffering from colorectal cancer which comprises determining an amount of whole-sized lactoferrin (μg/g feces) in the fecal sample by immunoassay utilizing a monoclonal antibody to whole-sized lactoferrin.

That is, lactoferrin in fecal samples of patients with colorectal cancer was subjected to gel filtration chromatography in which lactoferrin was measured by immunoassay utilizing polyclonal antibody (DAKOPATT, Denmark, referred to as DAKO hereinafter). The result clearly shows that lactoferrin has two kinds of molecular weights as shown in FIG. 11. The one is lactoferrin having a little less than 80,000 (referred to as "whole-sized lactoferrin" hereinafter) of which the peak is present in between fractions No. 10 and No. 15 by gel filtration chromatography as shown in FIG. 11, and the other is a half-sized of the former (referred to as "half-sized lactoferrin" hereinafter) of which the peak is present between fractions No. 25 and No. 30.

Then, the origin of the half-sized lactoferrin was studied as follows.

Firstly, lactoferrin extracted from leukocytes was subjected to gel filtration chromatography as described above in order to observe its molecular weight pattern and the result was shown in FIG. 12. Lactoferrin derived from neutrophilic leukocytes does not contain half-sized lactoferrin in an amount so much as in a fecal sample.

Then, we studied change of lactoferrin concentration in fecal specimen by treating with various pH values as follows. Liquid specimens of feces from a healthy person free from lactoferrin were prepared and purified lactoferrin was added thereto. The resultant specimens were adjusted to pHs 6, 4 and 2 and subjected to gel filtration chromatography in which lactoferrin was determined by immunoassay utilizing polyclonal antibody (DAKO). The result was shown in FIG. 13. The half-sized lactoferrin clearly increased as the pH values decreased.

In addition, digestion of lactoferrin with pepsin which is a digestive enzyme in a stomach was studied as follows.

Liquid specimens of feces from healthy persons free from lactoferrin were prepared and then purified lactoferrin was added thereto. The resultant liquid specimens were treated with pepsin. The result was shown in FIG. 14. It was observed that the half-sized lactoferrin almost alone was detected.

As shown in FIGS. 13 and 14, it was supposed that the whole-sized lactoferrin could be almost changed to the half-sized lactoferrin by treating with pepsin at pH 2. Therefore, the half-sized lactoferrin appears to be derived from lactoferrin in saliva which has been incompletely digested in a stomach to come out as the half-sized lactoferrin in feces, because there is no chance for lactoferrin to be exposed to pepsin or a strong acidity such as pH 2 at and after a small intestine.

Then, lactoferrin in saliva was determined as follows. Saliva was collected using OraSure (Epitope, Inc. Beaverton, Oreg.). Saliva with 1.75-fold dilution was diluted 10-fold with TBS (0.1 mole, pH 8.0) to prepare saliva specimens finally diluted 17.5-fold, which were used to measure lactoferrin by ELISA.

The result shows that lactoferrin concentration of salivary samples from 20 healthy subjects (7 men and 13 women) were 6.5±3.3 μg/ml (mean ± SD) on average, 10.8μg/ml at maximum and 2.4 μg/ml at minimum.

The amount of saliva per one day is 1,000 to 1,500 ml, and therefore, about 10 mg per day of lactoferrin was provided to a stomach. On the other hand, the upper value of lactoferrin in fecal samples of healthy persons is 2.4 μg/g feces (= 0.5 mg/200 g feces). In the light of this value and the result as shown in FIG. 11, it is strongly supposed that lactoferrin in saliva should not be completely digested in a stomach to give the half-sized lactoferrin in feces.

Then, three kinds of lactoferrin, i.e. lactoferrin previously treated at pH 2, lactoferrin previously treated with pepsin and whole-sized lactoferrin were digested by trypsin which is a digestive enzyme in a small intestine. The result was shown in FIG. 15. In each case, lactoferrin was not digested by trypsin so much and, in particular, lactoferrin previously treated with pepsin was hardly digested by trypsin. As understood from the result shown in FIG. 15, it is possible that lactoferrin incompletely digested in a stomach comes out as half-sized lactoferrin in feces, on the other hand, the whole-sized lactoferrin detected in feces was firstly released in a small or a large intestine.

Therefore, it is now found that only the whole-sized lactoferrin having molecular weight 80,000 in feces should be measured for screening of gastrointestinal tract disorders such as colorectal cancer with high probability thereof. The present invention was accomplished by the findings as above.

Thus, the object of the invention is to provide a screening test method for colorectal cancer by measurement of the whole-sized lactoferrin in feces.

According to the invention, only the whole-sized lactoferrin in feces is measured in order to find colorectal cancer with high probability in persons suspected of suffering from colorectal cancer.

Any immunological method can be used for measuring the amount of lactoferrin, it is preferred to use, for example, enzyme labelled immunoassay methods or latex agglutination.

In these cases, it is possible to screen colorectal cancer by using lactoferrin antibody which neither reacts with any lactoferrin previously exposed to acidity of pH about 2, nor with any lactoferrin previously reacted with pepsin, but reacts only with whole-sized lactoferrin.

The present invention is more specifically illustrated below.

Spleen lymphocytes which was injected with human lactoferrin were fused with mous myeloma cells to obtain hybridoma which produces anti-human lactoferrin monoclonal antibodies of which characteristics are shown in FIG. 16.

Monoclonal antibody of the present invention (referred to as monoclonal antibody M28 hereinafter) was selected from the produced monoclonal antibodies, which neither reacts with any lactoferrin previously exposed to acidity of pH about 2, nor with any lactoferrin previously treated with pepsin, but reacts only with whole-sized lactoferrin.

FIG. 17 shows the reactivities of polyclonal antibodies (DAKO), monoclonal antibodies M28 of the present invention and another monoclonal antibodies (M267) with the identical fecal sample which was obtained from a patient with colorectal cancer.

FIG. 18 shows the reactivities of polyclonal antibodies (DAKO) and monoclonal antibodies (M28) with lactoferrin which was extracted from neutrophilic leukocytes. The results show that DAKO and M28 reacted in the same manner with lactoferrin derived from neutrophilic leukocytes.

A fecal liquid sample of a healthy person was prepared and then purified lactoferrin was added thereto to give fecal liquid specimens. The liquid specimens were adjusted to pH at 8, 6, 4 and 2 and subjected to gel filtration chromatography. FIGS. 19D, 19C, 19B and 19A respectively show the reactivities of DAKO and M28 with purified lactoferrin in fecal specimens from a healthy subject at pHs 8, 6, 4 and 2. Polyclonal antibody (DAKO) reacted with lactoferrin at pH 2, but monoclonal antibody M28 reacted in a different manner from polyclonal antibody when the pH of the solution decreased i.e. the acidity of the solution became stronger. That is, FIGS. 19D, 19C, 19B and 19A show that monoclonal antibody M28 does not react with half-sized lactoferrin.

FIG. 20 shows the reactivities of monoclonal antibody M28 and polyclonal antibody (DAKO) with the half-sized lactoferrin obtained after treating with pepsin.

FIG. 21 shows the reactivities of monoclonal antibody M28 and polyclonal antibody (DAKO) with fecal specimens from a patient With colorectal cancer. The result shows that when the monoclonal antibody M28 was used, only the whole-sized lactoferrin was detected.

FIGS. 22A and 22B show the results of measurement of lactoferrin concentrations in fecal specimens from 231 healthy persons using the polyclonal antibody (DAKO) and the monoclonal antibody M28. When the polyclonal antibody (DAKO) was used, the cut-off value is 114 ng/ml corresponding to 2.4 µg/g feces, on the other hand, when the monoclonal antibody M28 was used, the cut-off value is 45 ng/ml corresponding 1.0 µg/g feces, i.e. less than a half of that for the polyclonal antibody. The results clearly show that the use of monoclonal antibody M28 improves the accuracy of the measurement of the whole-sized lactoferrin concentration.

FIG. 23 shows the results of measurement of lactoferrin concentrations (µg/g feces) in the fecal specimens from patients with colorectal cancer using the polyclonal antibody (DAKO) and the monoclonal antibody M28. The results of the measurement shows an adequate correlation, and it was recognized that the use of the monocloanal antibody M28 improves the accuracy of the measurement of lactoferrin concentration. In addition, the cut-off value in the case of using a monoclonal antibody M28 is about 1 µg/g feces and that value when the polyclonal antibody used is 2.4 µg/g feces.

The measurement of lactoferrin concentrations as above stated was conducted by ELISA as described in Example 2. The lactoferrin measurement using the monoclonal antibody M28 and polyclonal antibody (DAKO) in forward sandwich method by ELISA was described fin Example 7.

Monoclonal antibody M28 was produced from mice by conventional methods which are commonly used in the art and polyclonal antibody (DAKO) is commercially available.

BRIEF DESCRIPTION OF THE DRAWINGS

FIGS. 19D, 19C, 19B and 19A respectively show reactivities of polyclonal antibody (DAKO) and monoclonal antibody M28 with lactoferrin in a fecal sample at pH 8, 6, 4 and 2 by gel filtration chromatography and ELISA.

EXPERIMENT

Experiment 1

Effect of bleeding

Blood was collected from 10 normal subjects for the measurement of lactoferrin in blood plasma and in whole blood. Twelve milligrams of EDTA/2K per 1 ml of blood was added to the blood sample in order to avoid activation of polymorphonuclear leukocytes and to measure lactoferrin in blood plasma accurately.

To measure lactoferrin in whole blood, the sample was prepared as follows: 20 μl of 10% Triton X-100 (WAKO Junyaku, Japan) was added to 200 μl whole blood and mixed well to lyse blood cells; then this sample was diluted 100-fold with Tris-saline buffer. The measurement of lactoferrin in blood was carried out in the same way as for feces. A blood plasma sample diluted 10-fold with Tris-saline buffer was used to measure lactoferrin in blood plasma.

The lactoferrin concentration in whole blood was 6.88± 2.35 μg/ml. The lactoferrin concentration in blood plasma of 10 normal subjects was 86.4±28.5 ng/ml (mean±SD). The fecal lactoferrin concentration with mixture of 250 μl of whole blood was 2.1–2.3 μg/g feces, which was below the upper reference value (this corresponds to the case of 25 ml of blood mixed with 100 g of feces).

Experiment 2

Specificity of the antibody

Figure 1:
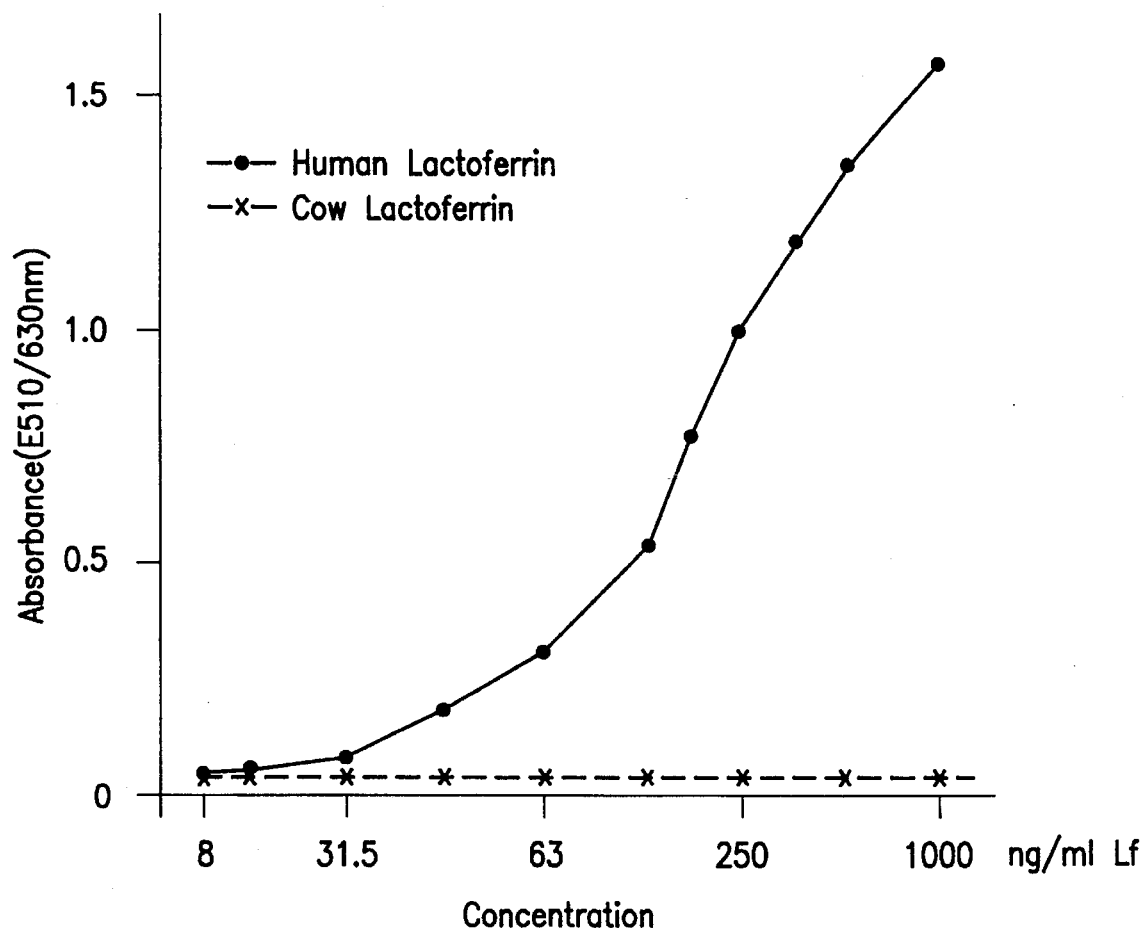
FIG. 1 shows specificity of anti-human lactoferrin antibody.

ELISA was utilized to study the sensitivity of an anti-human-lactoferrin antibody (DAKOPATT, 089) to human lactoferrin (Sigma, L-3770), and to bovine lactoferrin from milk (Sigma, L-9507). The results showed that the antibody reacted with human lactoferrin, but not with bovine milk lactoferrin (FIG. 1).

Experiment 3

Stability of lactoferrin and hemoglobin in feces

Figure 2:
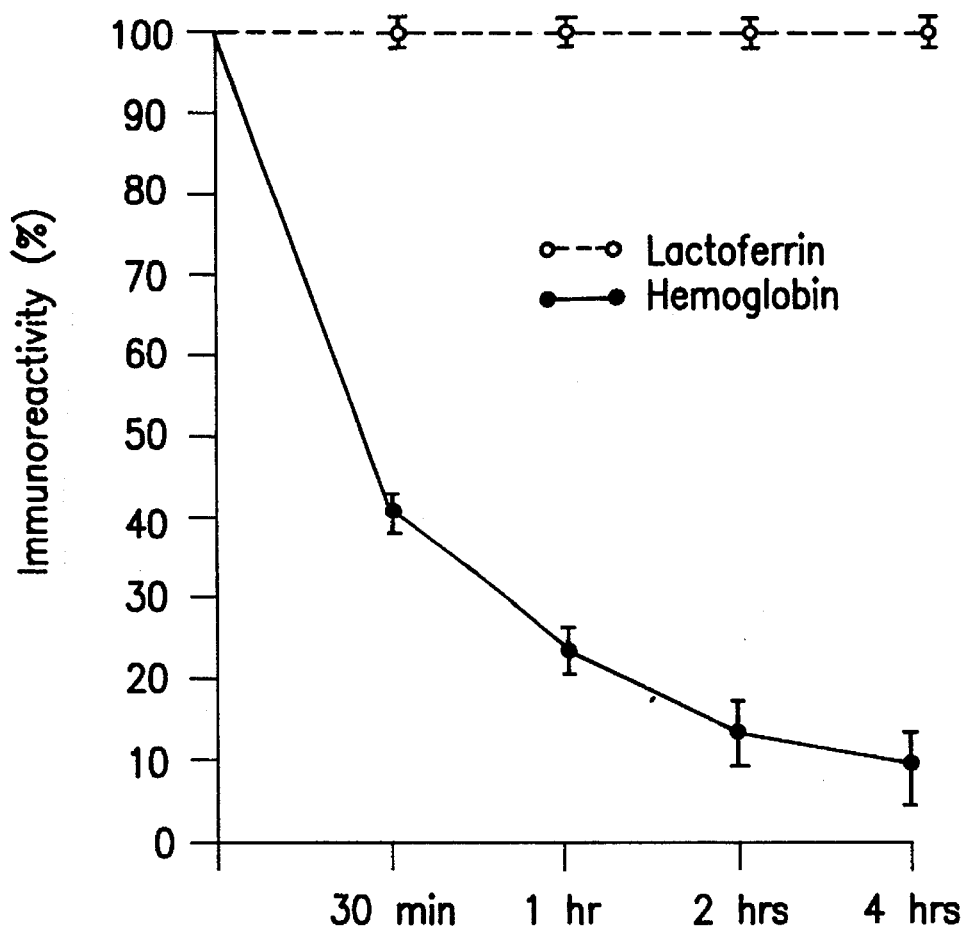
FIG. 2 shows stability of lactoferrin and hemoglobin in feces at 37° C.
Figure 3:
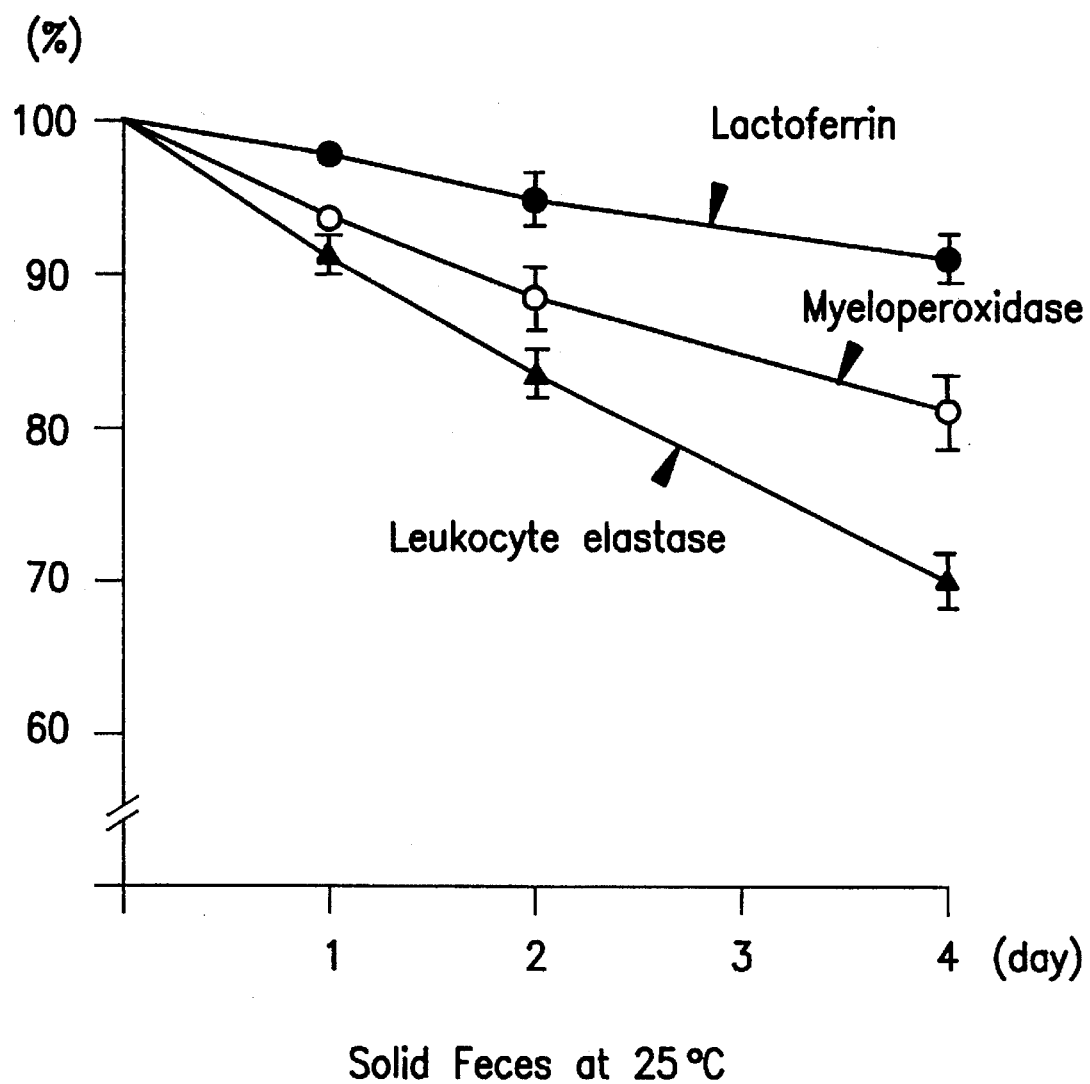
FIG. 3 shows stability of lactoferrin and hemoglobin in solid feces at 25° C.

Human lactoferrin and human hemoglobin were added to fecal specimens made from feces of normal subjects (1 g of feces was homogenized in 5 ml of deionized water, to which were added whole blood and human lactoferrin (Sigma, U.S.A.) so that the sample contained 1 mg/ml of hemoglobin and 1 μg/ml of lactoferrin); then samples were incubated at 37° C. and the hemoglobin (Uchida K, Matsuse R, Miyachi N, et al. Immunochemical detection of human blood in feces. Clin Chim Acta 1990;189:267–274) and lactoferrin concentration of samples were measured by the ELISA method 30 minutes, 1 hour, 2 hours and 4 hours after incubation. Hemoglobin concentration fell rapidly whereas there was little change in lactoferrin (FIG. 2). The stability of lactoferrin, myeloperoxidase and polymorphonuclear leucocyte elastase were also studied on solid fetes at 25° C. (FIG. 3).

DETAILED DESCRIPTION OF THE PREFERRED EMBODIMENTS

The nonlimiting examples were given as follows:

EXAMPLE

Example 1

1. Clinical samples (a) The control group consisted of a total of 35 subjects, 17 with no demonstrated abnormality in the upper gastrointestinal tract, as confirmed by endoscopy, and no abnormality in the colon, as confirmed either by coloscopic examination or barium enema, and 18 apparently healthy subjects;
   (i). 16 patients with colon polyps.
   (ii). 13 patients with colorectal cancer (1 early stage, 12 advanced stage).
   (iii). 28 patients with ulcerative colitis (38 samples from patients with active ulcerative colitis and 20 samples from patients with inactive ulcerative colitis).

(iv). 18 patients with Crohn's disease (36 samples from patients with active Crohn's disease and 16 samples from patients with inactive disease)

2. Collection of feces

Subjects were asked to defecate directly into a polystyrene container (diameter 15 cm, depth 12 cm) which could be sealed, and to collect all feces. The collected feces were immediately stored in a refrigerator at 4° C. The feces were mixed well using a handmixer set into the cap of the container. When mixing was difficult, a small amount of deionized water was added.

3. Preparation of fecal specimen

Twenty milligrams of feces was collected from the container, measured and mixed into 2 ml of TBS buffer (0.1 mol/l Tris-HCl buffer containing 0.1 mol/l of NaCl at pH 8.0).

Example 2

1. ELISA of lactoferrin

Anti-human-lactoferrin antibody (DAKOPATTS, Denmark) was added to each well of a 96-well polystyrene microplate (SUMILON, Japan) and allowed to stand until adsorption occurred. That is, 100 µl of 0.1 mol/l Tris-buffer (pH 8.4) containing 5 µg/ml anti-human-lactoferrin antibody was placed in each well and left overnight at 4° C.

Anti-human-lactoferrin antibody (DAKOPATT, Denmark) was labeled with alkaline phosphatase (Boehringer Mannheim, F.R.G.) by the periodic acid Schiff stain method (Nakane P K, Kawaoi A. Peroxidase-labeled antibody, a new method of conjugation. J Histo Chem Cytochem 1974;22:1084–1091). ELISA of lactoferrin was conducted as follows: 100 µl of 1% BSA (Boehringer Mannheim, F.R.G.) and TBS buffer were separately injected into each well of the microplate, to which 50 µl of fecal specimen was added. The mixture was allowed to stand at 37° C. for one hour (first reaction) and then washed three times with deionized water containing 0.05% of Tween-20. Then 100 µl of alkaline phosphatase-labeled anti-human-lactoferrin antibody solution prepared with 1% of BSA Tris-saline buffer was added to each well, allowed to react at 37° C. for another hour (second reaction) and washed three times. The Kind -King method (Kind RPN, King EL. Estimation of plasma phosphatase by determination of hydrolyzed phenol with amino-antipyrine. J Clin Path 1954;7:323–326) was used for the measurement of alkaline phosphatase. A substrate buffer ((disodium phenylphosphate: 0.215 g (WAKO Junyaku, Japan) and 4-aminoantipyrine: 0.09 g (WAKO Junyaku, Japan)) was dissolved in 100 ml of carbonate buffer solution (0.05M, pH: 10.15) and added into each well. This was allowed to react at 37° C. for 30 minutes. Then 100 µl of coloring reagent (a mixture of 2.6 g boric acid (WAKO Junyaku, Japan) dissolved in 200 ml of deionized water and 0.38 g potassium ferricyanide (WAXO Junyaku, Japan)) was added to each well to produce a color reaction. The color of each well was assessed by determining absorbance at 510/630 nm with a microplate photometer (Sanko Junyaku, Japan). Lactoferrin concentration in the fecal specimens was obtained from a lactoferrin quantification curve. (Fecal lactoferrin concentration (µg/g feces) was the value of the lactoferrin concentration obtained from the LF quantification curve (ng/ml) multiplied by the dilution factor 100). (See Uchida et al., The Japanese Journal of Clinical Pathology, 40 (add.), 61, 1992, and Uchida et al., Journal of Analytical Bio-Science, 16(1), 87, 1993.)

2. Fecal human lactoferrin quantification curve

Figure 4:
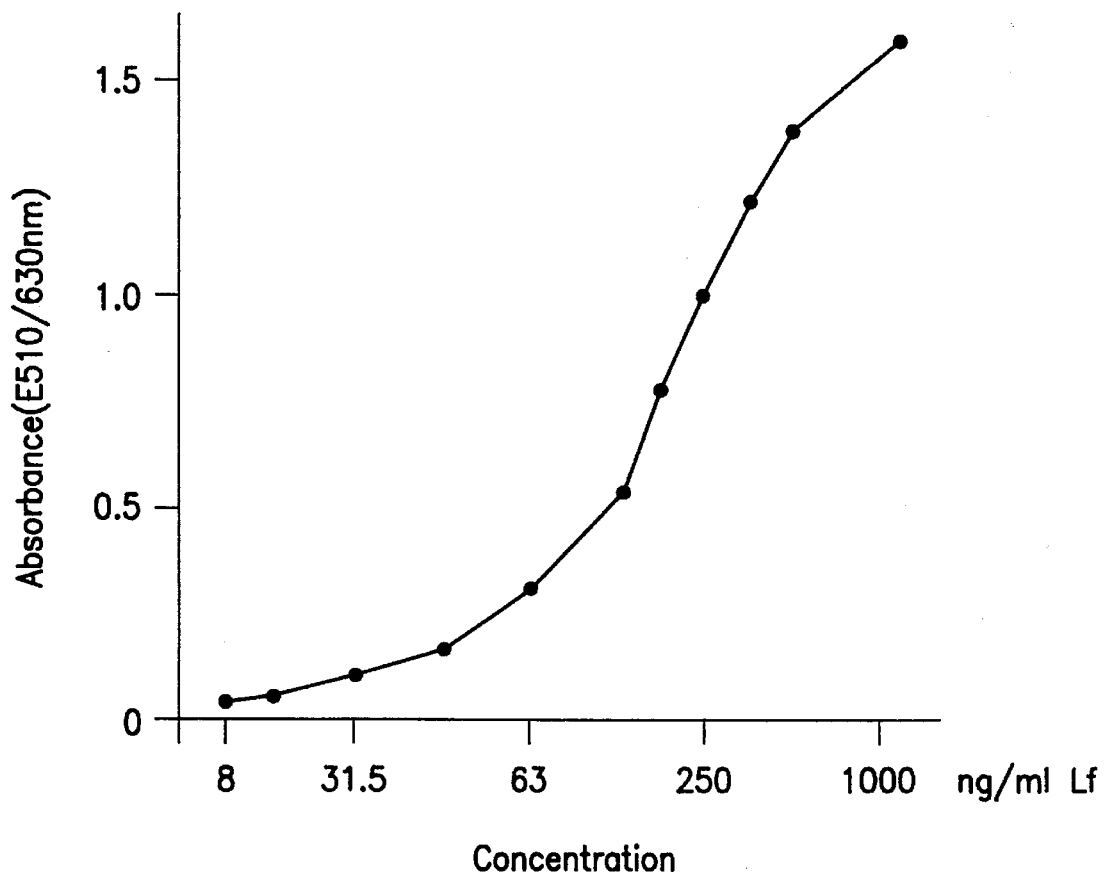
FIG. 4 shows a quantification curve of human lactoferrin by enzyme-linked immunosorbent assay.

Using human lactoferrin (Sigma, U.S.A.) as the standard, a calibration curve is shown in FIG. 4. The assay range was 10.0 to 1000.0 ng/ml lactoferrin concentration.

3. Results (1). The average lactoferrin concentration of 35 subjects in the control group was 0.75±0.83 µg/g feces (mean±SD), and the upper reference value (mean of control group+ 2SD) was 2.4 µg/g feces.

(2). The average lactoferrin concentration of the patients with active ulcerative colitis was 307.4±233.9 µg/g feces, and all of the 38 patients showed values of more than 2.4 µg/g feces. The reading for the patients with inactive ulcerative colitis was 63.3±144.6 µg/g feces, and that for 15 patients among 20 (75.0%) was more than 2.4 µg/g feces.

(3). The average concentration for the patients with active Crohn's disease was 191.7±231.1 µg/g feces, and all of the 36 patients showed values of more than 2.4 µg/g feces. The average value for the patients with inactive Crohn's disease was 25.1±38.6 µg/g feces, and 15 patients among 16 (93.8%) had values exceeding 2.4 µg/g feces.

(4). That of the patients with colon polyps was 6.1±9.1 µg/g feces, and 7 patients among the 16 (43.8%) showed a concentration of more than 2.4 µg/g feces.

Figure 7:
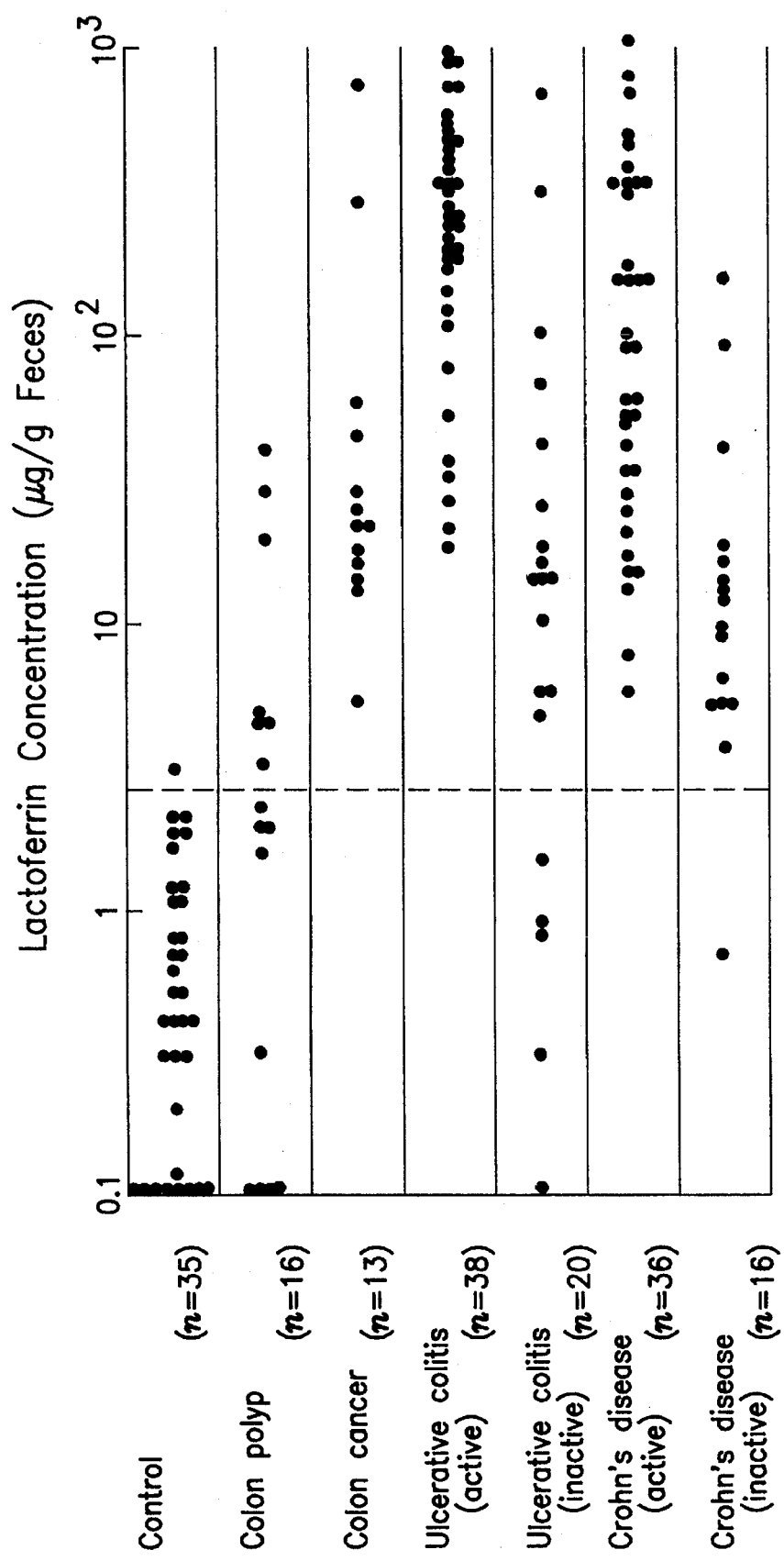
FIG. 7 shows lactoferrin concentration in feces from patient with ulcerative colitis, Crohn's disease, colon cancer, those with colon polyp and control patients (µg/g feces). The dotted line indicates the upper reference value (mean of control group+2 SD).

(5). That of the patients with colorectal cancer was 89.7±82.4 µg/g feces, and all of the 13 colorectal cancer patients had concentration of more than 2.4 µg/g feces (FIG. 7).

Example 3

1. ELISA of myeloperoxidase

The procedure of the ELISA of myeloperoxidase was carried out as described in Example 2, expect that anti-human myeloperoxidase antibody (DAKOPATTS, Denmark) was used instead of anti-human lactoferrin antibody.

2. Fecal human myeloperoxidase quantification curve

Figure 5:
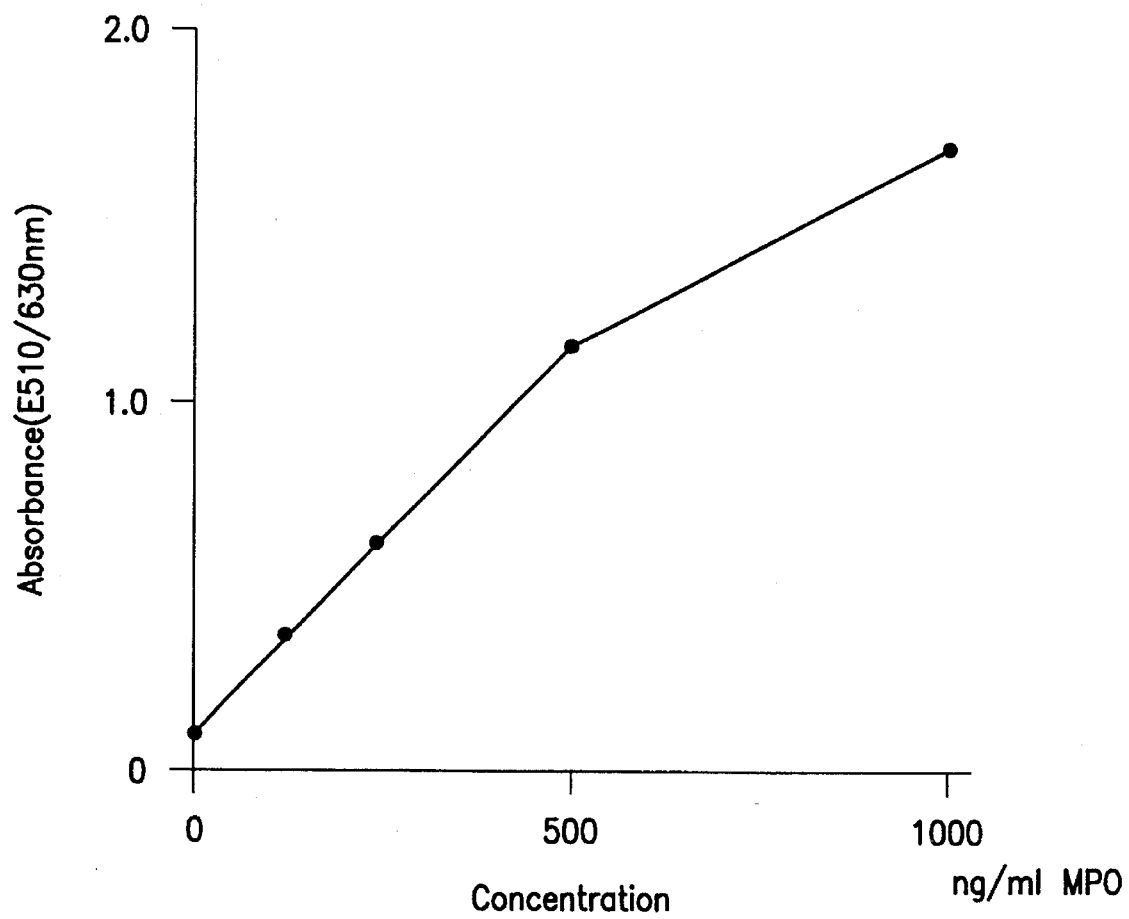
FIG. 5 shows a quantification curve of human myeloperoxidase by enzyme-linked immunosorbent assay.

Using human myeloperoxidase (Sigma, U.S.A.) as the standard, a calibration curve is shown in FIG. 5. The assay range was 0 to 1000.0 ng/ml myeloperoxidase concentration.

3. Results (1). The average myeloperoxidase concentration of 35 subjects in the control group was 2.4±0.9 µg/g feces (mean± SD), and the upper reference value (mean of control group+ 2SD) was 4.2 µg/g feces.

(2). The average myeloperoxidase concentration of the patients with active ulcerative colitis was 206.2±196.6 µg/g feces, and 36 patients among the 38 patients showed values of more than 4.2 µg/g feces. The reading for the patients with inactive ulcerative colitis was 37.8±89.6 µg/g feces, and that for 17 patients among 20 (85.0%) was more than 4.2 µg/g feces.

(3). The average concentration for the patients with active Crohn's disease was 191.7±231.1 µg/g feces, and all of the 36 patients showed values of more than 2.4 µg/g feces. The average value for the patients with inactive Crohn's disease was 25.1±38.6 µg/g feces, and 15 patients among 16 (93.8%) had values exceeding 2.4 µg/g feces.

(4). That of the patients with colon polyps was 5.9±7.8 µg/g feces, and 7 patients among the 16 (43.8%) showed a concentration of more than 4.2 µg/g feces.

Figure 8:
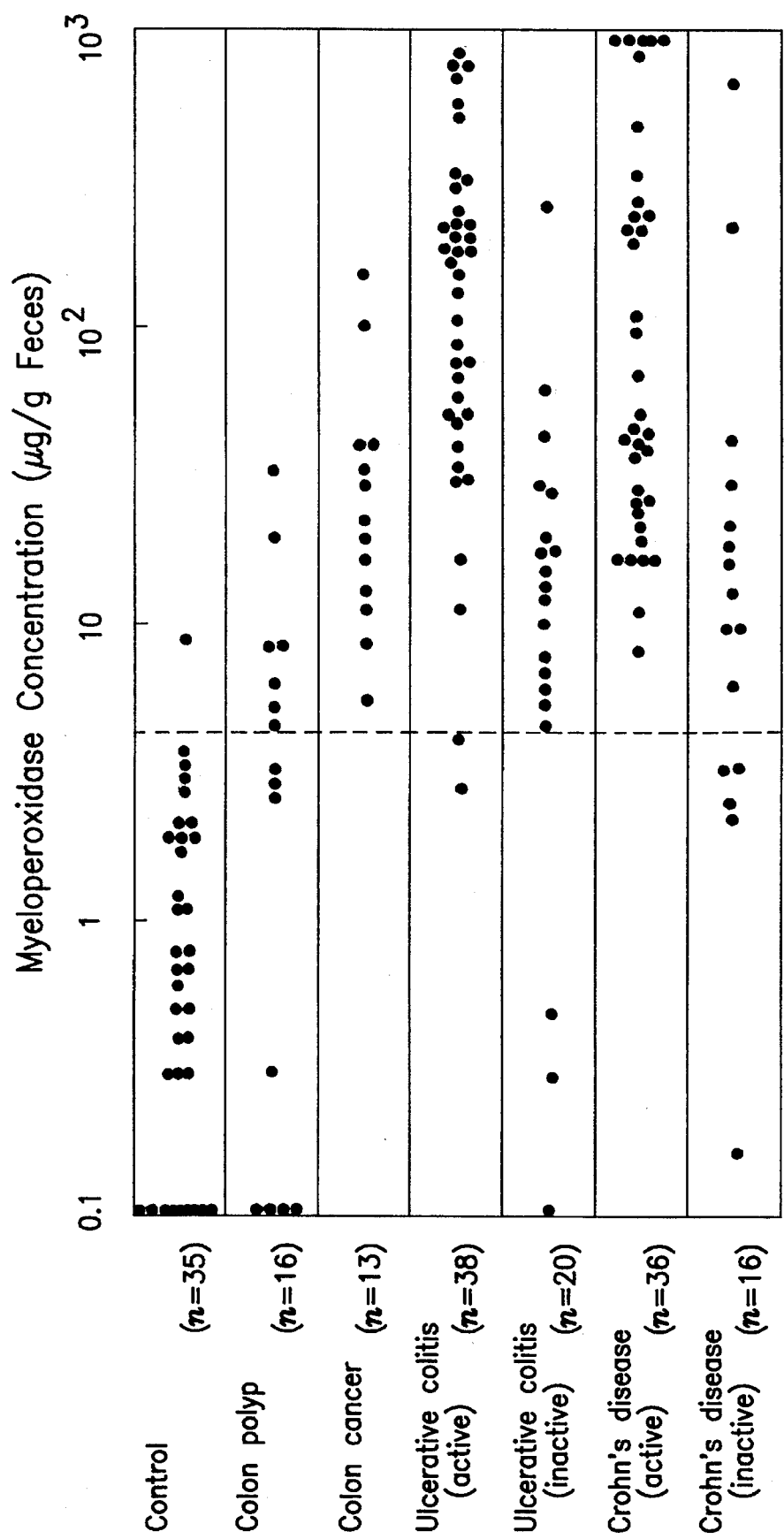
FIG. 8 shows myeloperoxidase concentration in feces from patient with ulcerative colitis, Crohn's disease, colon cancer, those with colon polyp and control patients (µg/g feces). The dotted line indicates the upper reference value (mean of control group+2 SD).

(5). That of the patients with colorectal cancer was 72.3±68.2 µg/g feces, and all of the 13 colorectal cancer patients had concentration of more than 4.2 µg/g feces (FIG. 8).

Example 4

1. ELISA of polymorphonuclear leucocyte elastase

The procedure of the ELISA of polymorphonuclear leucocyte elastase was carried out as described in Example 2, except that anti-human polymorphonuclear leucocyte elastase antibody (DAKOPATTS, Denmark) was used instead of anti-human lactoferrin antibody (see Uchida et al., The Japanese Journal of Clinical Pathology, 40(add.), 61, 1992).

2. Fecal human polymorphonuclear leucocyte elastase quantification curve

Figure 6:
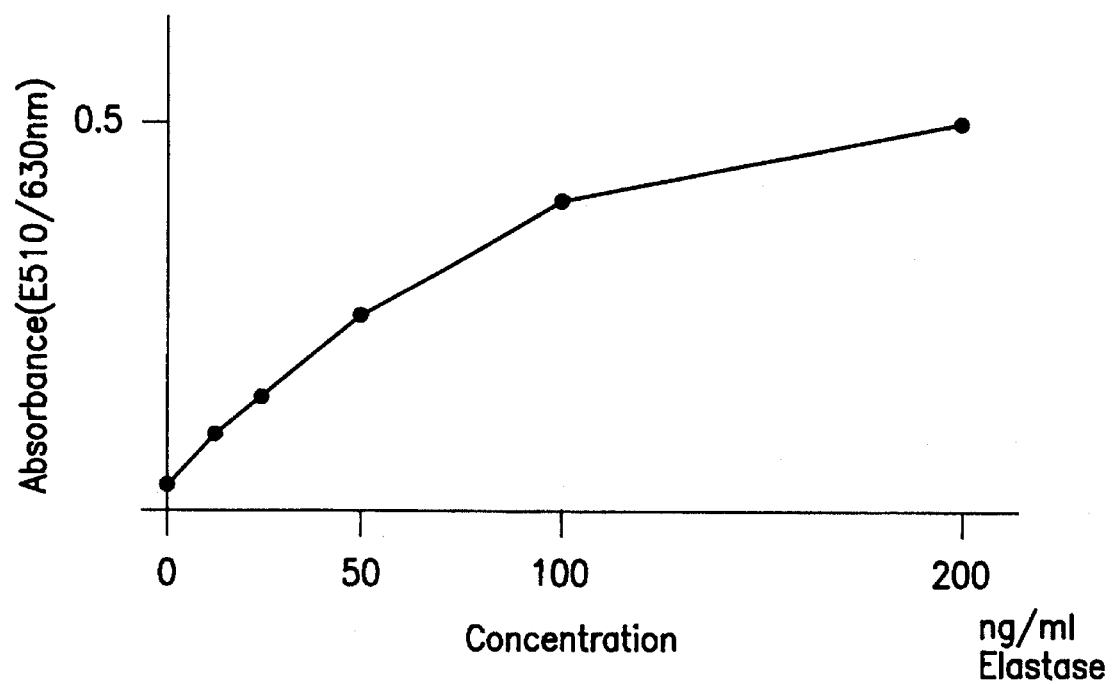
FIG. 6 shows a quantification curve of human polymorphonuclear leucocyte elastase by enzyme-linked immunosorbent assay.

Using human polymorphonuclear leucocyte elastase (Sigma, U.S.A.) as the standard, a calibration curve is shown in FIG. 6. The assay range was 0 to 200.0 ng/ml polymorphonuclease leucocyte elastase concentration.

3. Results (1). The average polymorphonuclear leucocyte elastase control group was 0.7±0.4 μg/g feces (mean ± SD), and the upper reference value (mean of control group + 2SD) was 1.5 μg/g feces.

(2). The average polymorphonuclear leucocyte elastase concentration of the patients with active ulcerative colitis was 52.2±41.3 μg/g feces, and 37 patients among the 38 patients (97.4%) showed values of more than 1.5 μg/g feces. The reading for the patients with inactive ulcerative colitis was 12.8±9.6 μg/g feces, and that for 15 patients among 20 (75.0%) was more than 1.5 μg/g feces.

(3). The average concentration for the patients with active Crohn's disease was 35.6±32.3 μg/g feces, and 35 patients among the 36 patients (97.2%) showed values of more than 1.5 μg/g feces. The average value for the patients with inactive Crohn's disease was 13.4±10.3 μg/g feces, and 12 patients among 16 (75.0%) had values exceeding 1.5 μg/g feces.

(4). That of the patients with colon polyps was 1.2±1.1 μg/g feces, and 11 patients among the 16 (31.2%) showed a concentration of more than 1.5 μg/g feces.

Figure 9:
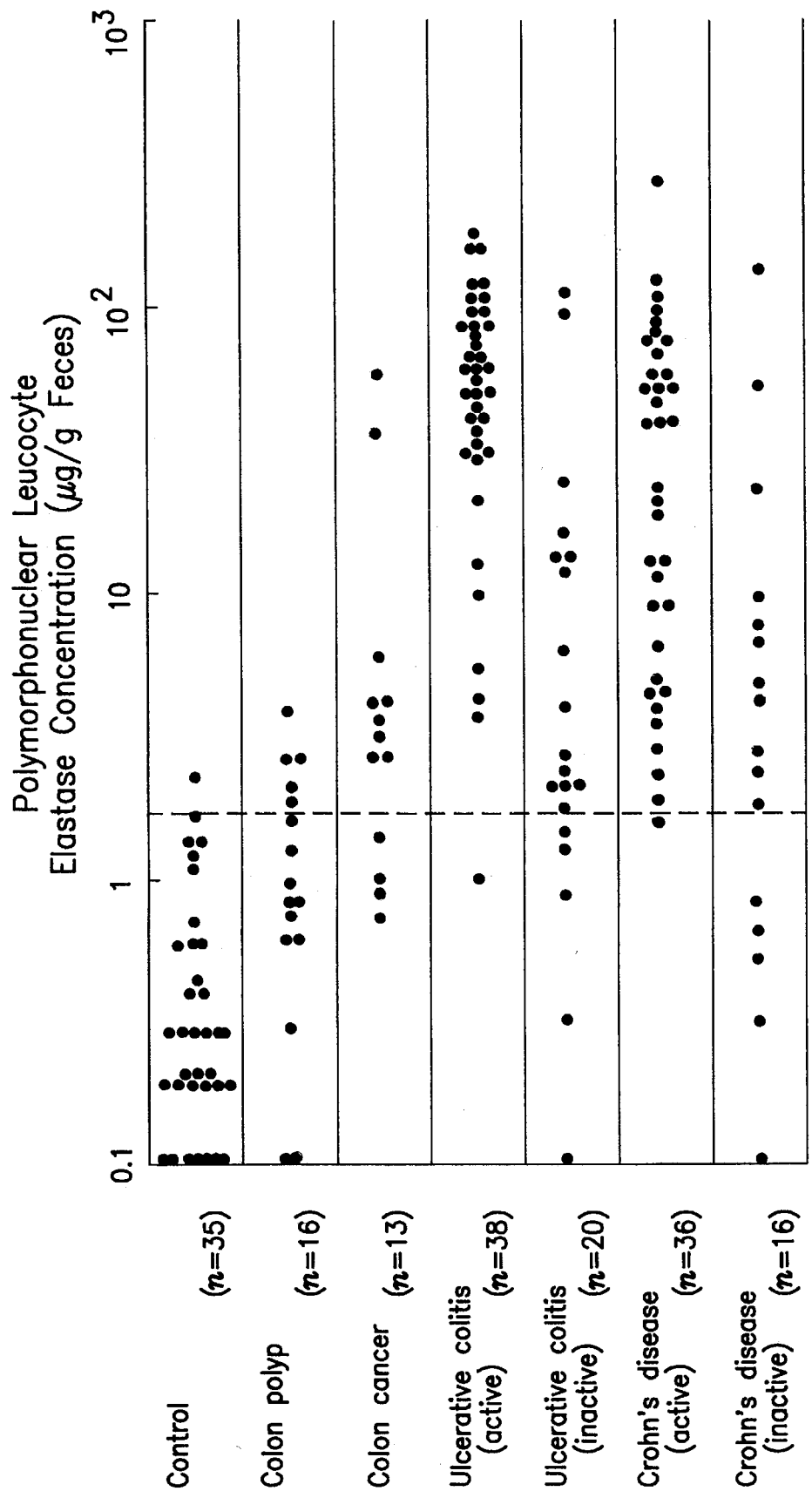
FIG. 9 shows polymorphonuclear leucocyte elastase concentration in feces from patient with ulcerative colitis, Crohn's disease, colon cancer, those with colon polyp and control patients (μg/g feces). The dotted line indicates the upper reference value (mean of control group+2SD).

(5). That of the patients with colorectal cancer was 5.2±4.1 μg/g feces, and 9 patients among the 13 colorectal cancer patients (69.3%) had concentration of more than 1.5 μg/g feces (FIG. 9).

Example 5

1. Immunochemical occult blood test

Immunochemical occult blood test was determined by an 1 in house ELISA as described in Uchida K, Matsuse R, Miyachi N, et al. Immunochemical detection of human blood in feces. Clin Chim Acta 1990;189:267–274 and Turuncn M J, Liewendahl K, Partanen P, Aldercreutz H. Immunological detection of fecal occult blood in colorectal cancer (see Uchida et al., Clin. Chim. Acta. 189, 267, 1990).

2. Results

Figure 10:
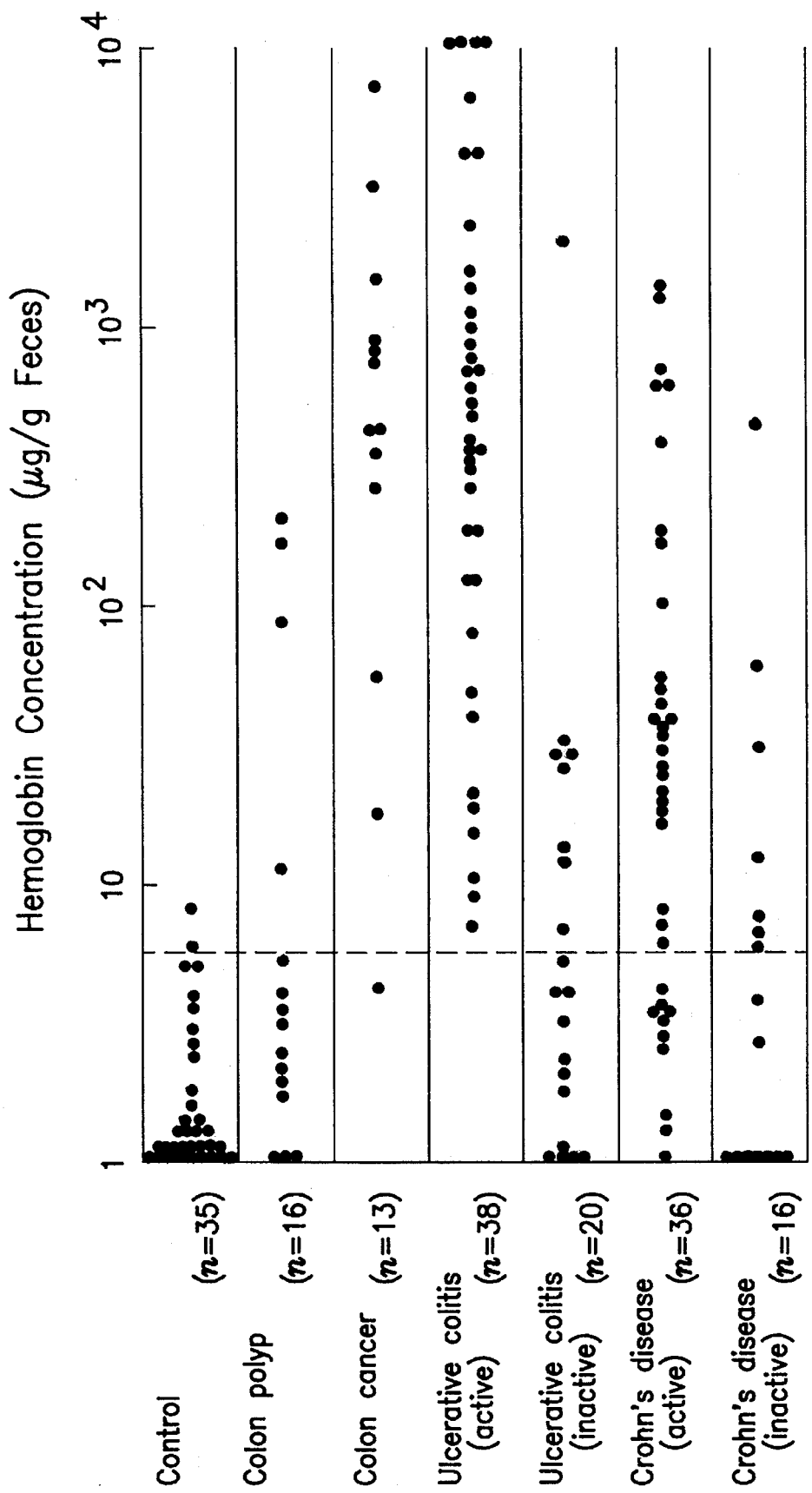
FIG. 10 shows hemoglobin concentration in feces from patient with ulcerative colitis, Crohn's disease, colon cancer, those with colon polyp and control patients (μg/g feces). The dotted line indicates the upper reference value (mean of control group+2SD).
Figure 11:
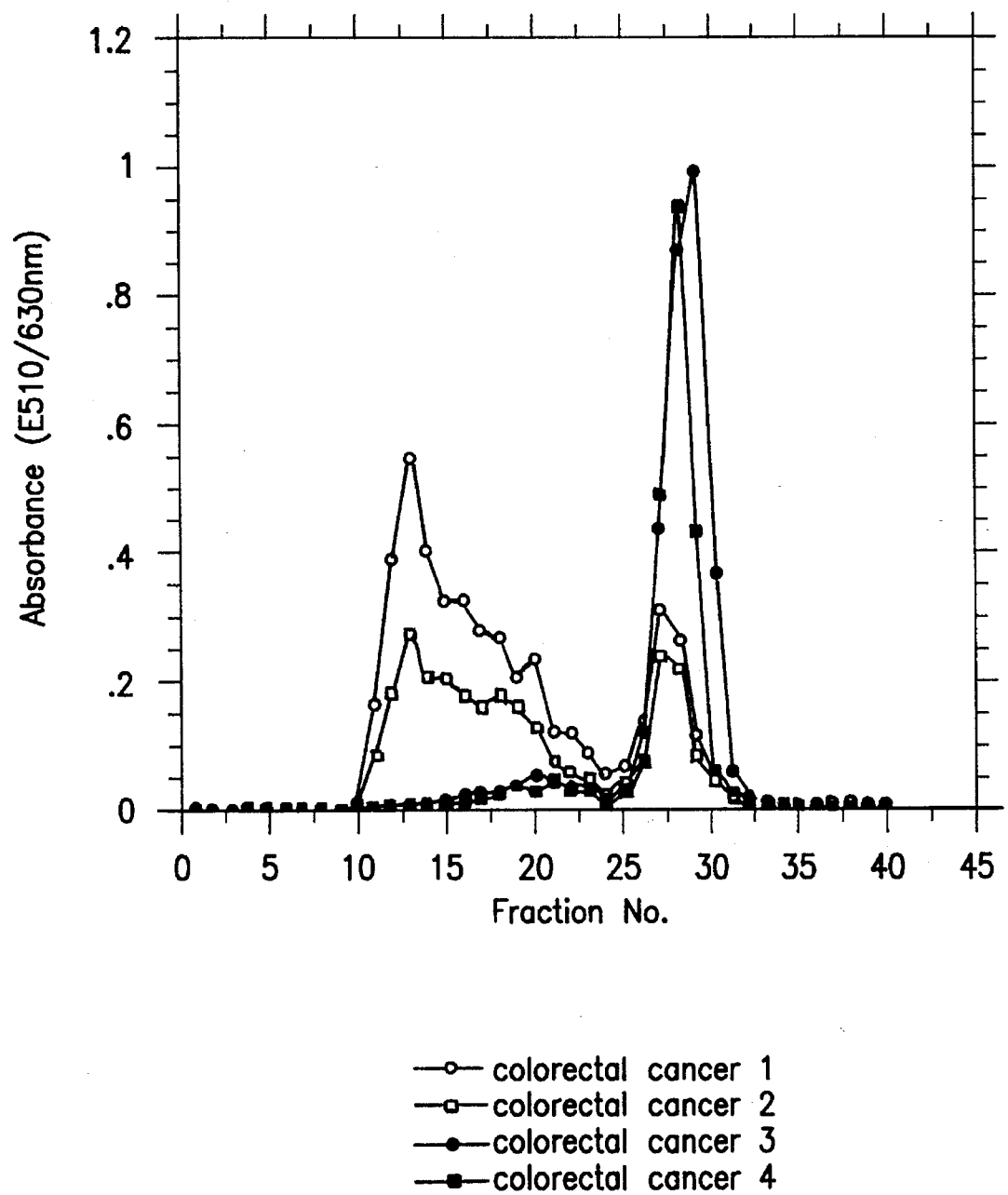
FIG. 11 shows molecular weight patterns of lactoferrin in fecal samples of colorectal cancer by gel filtration chromatography and ELISA using polyclonal anti-human-lactoferrin antibody.
Figure 12:
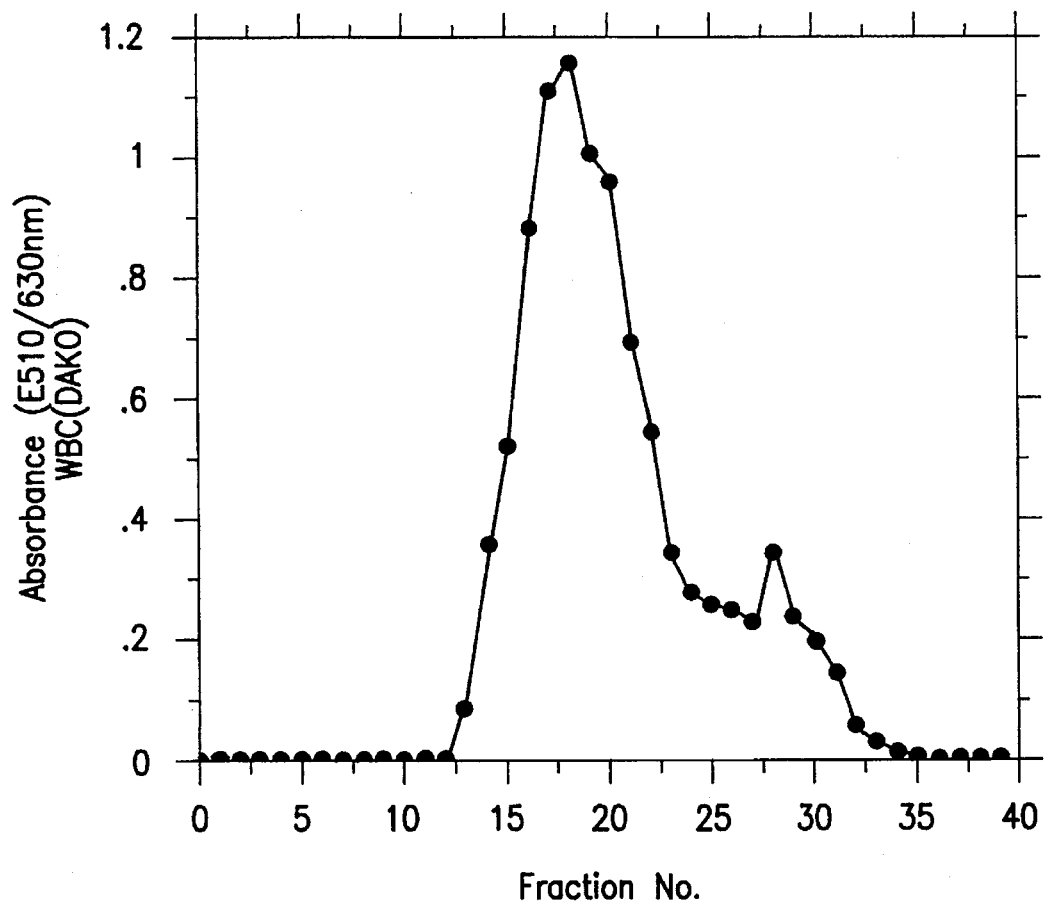
FIG. 12 shows a molecular weight pattern of lactoferrin derived from neutrophilic leukocytes by gel filtration chromatography and ELISA using DAKO.
Figure 13:
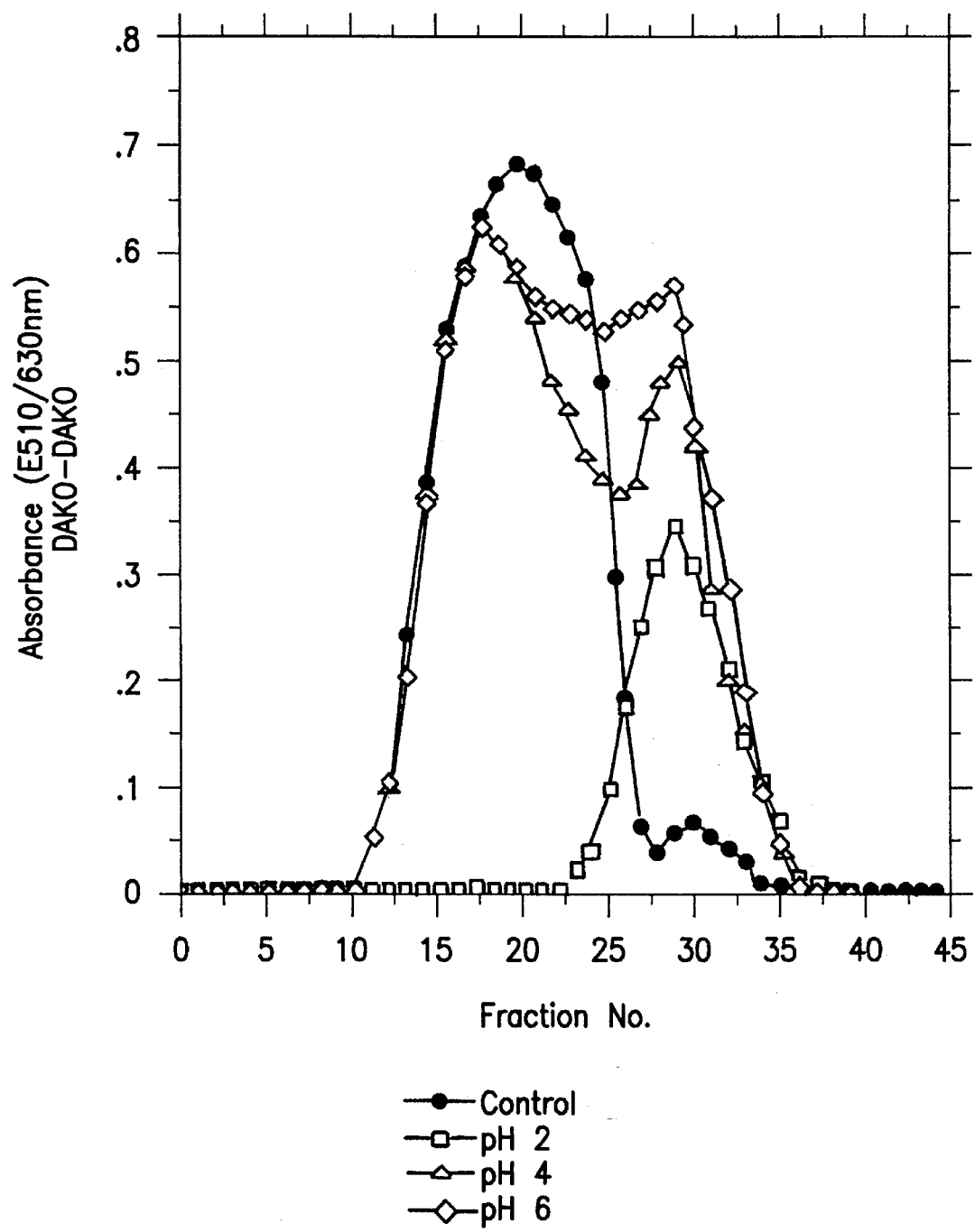
FIG. 13 shows molecular weight patterns of lactoferrin in fecal samples treated at pH 2 to 6 by gel filtration chromatography and ELISA using DAKO.
Figure 14:
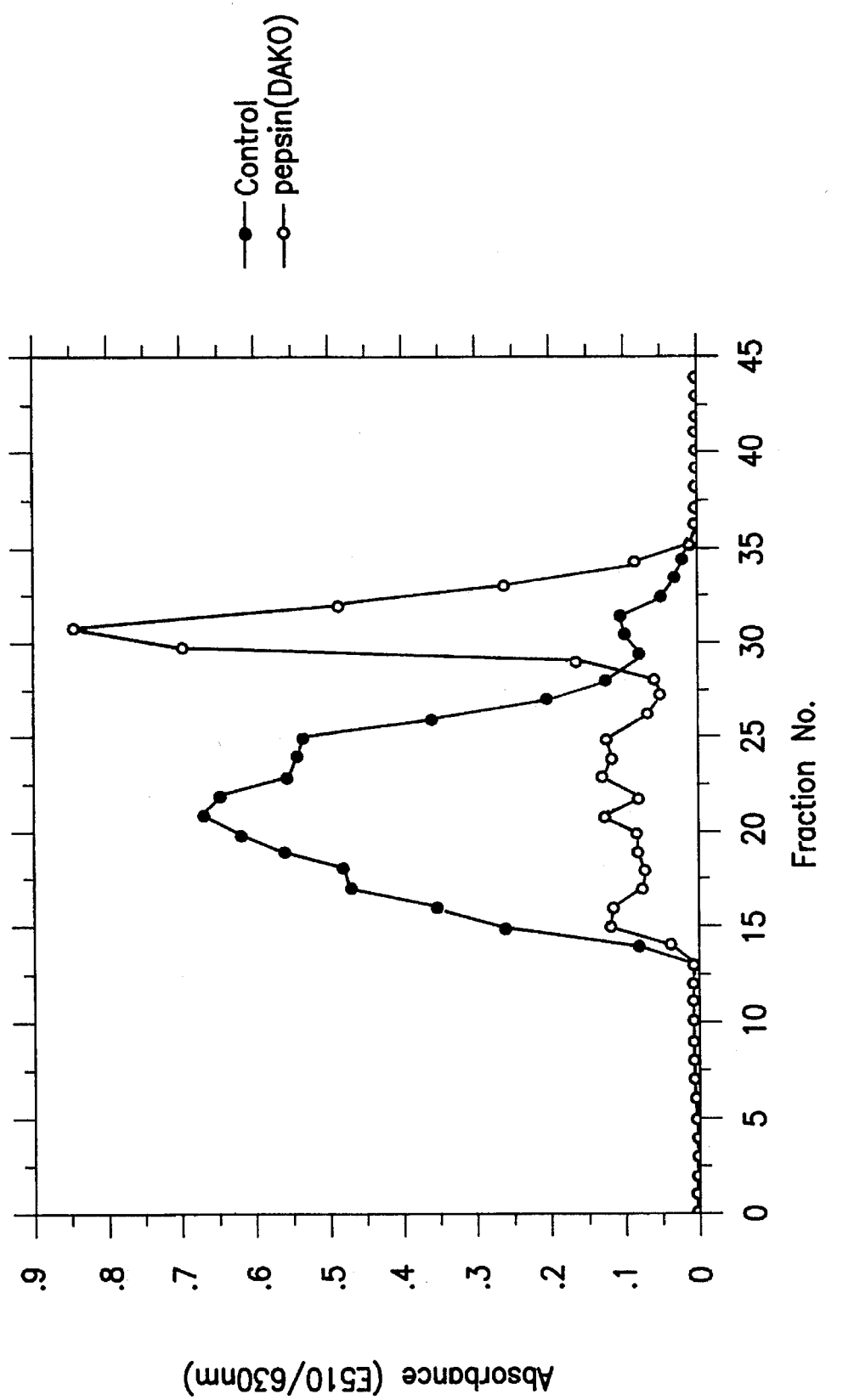
FIG. 14 shows molecular weight patterns of lactoferrin treated with pepsin by gel filtration chromatography and ELISA using DAKO.
Figure 15:
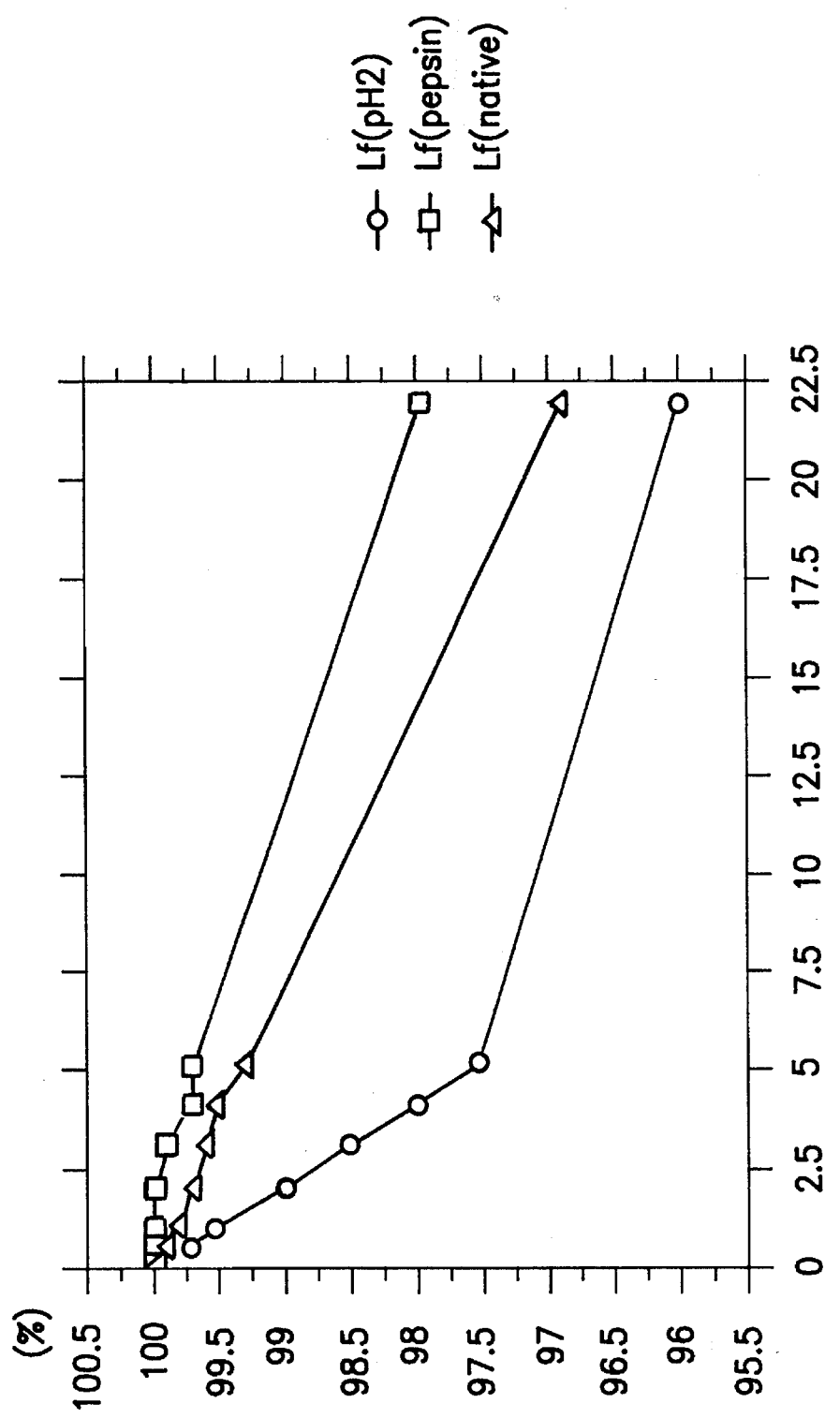
FIG. 15 shows digestion of lactoferrin treated at pH 2, lactoferrin treated with pepsin and whole-sized lactoferrin by trypsin.
Figure 16:
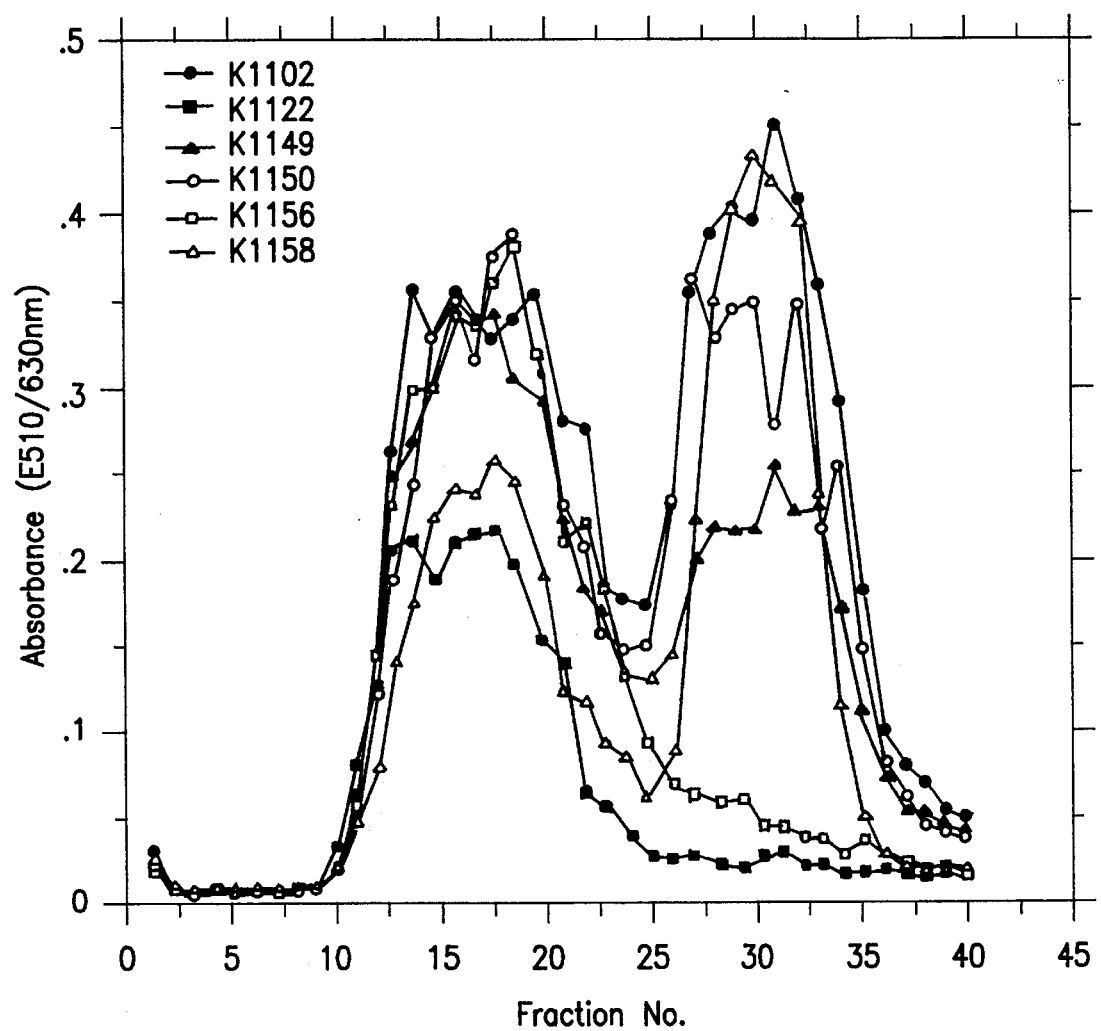
FIG. 16 shows reactivities of various monoclonal antibodies with lactoferrin in a fecal sample by gel filtration chromatography and ELISA.
Figure 17:
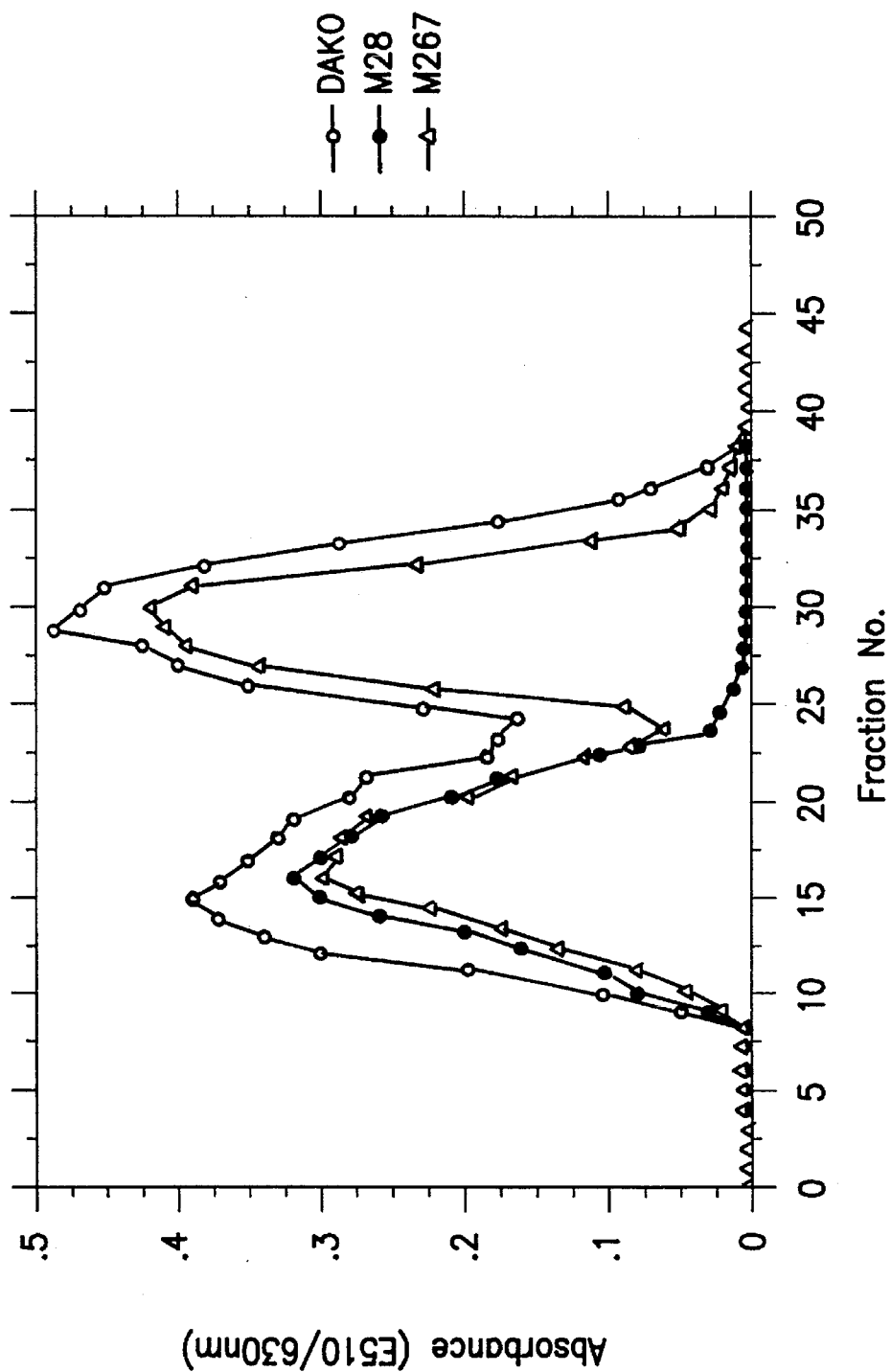
FIG. 17 shows reactivities of monoclonal antibody M28, monoclonal antibody M267 and polyclonal antibody (DAKO) with lactoferrin in a fecal sample by gel filtration chromatography and ELISA.
Figure 18:
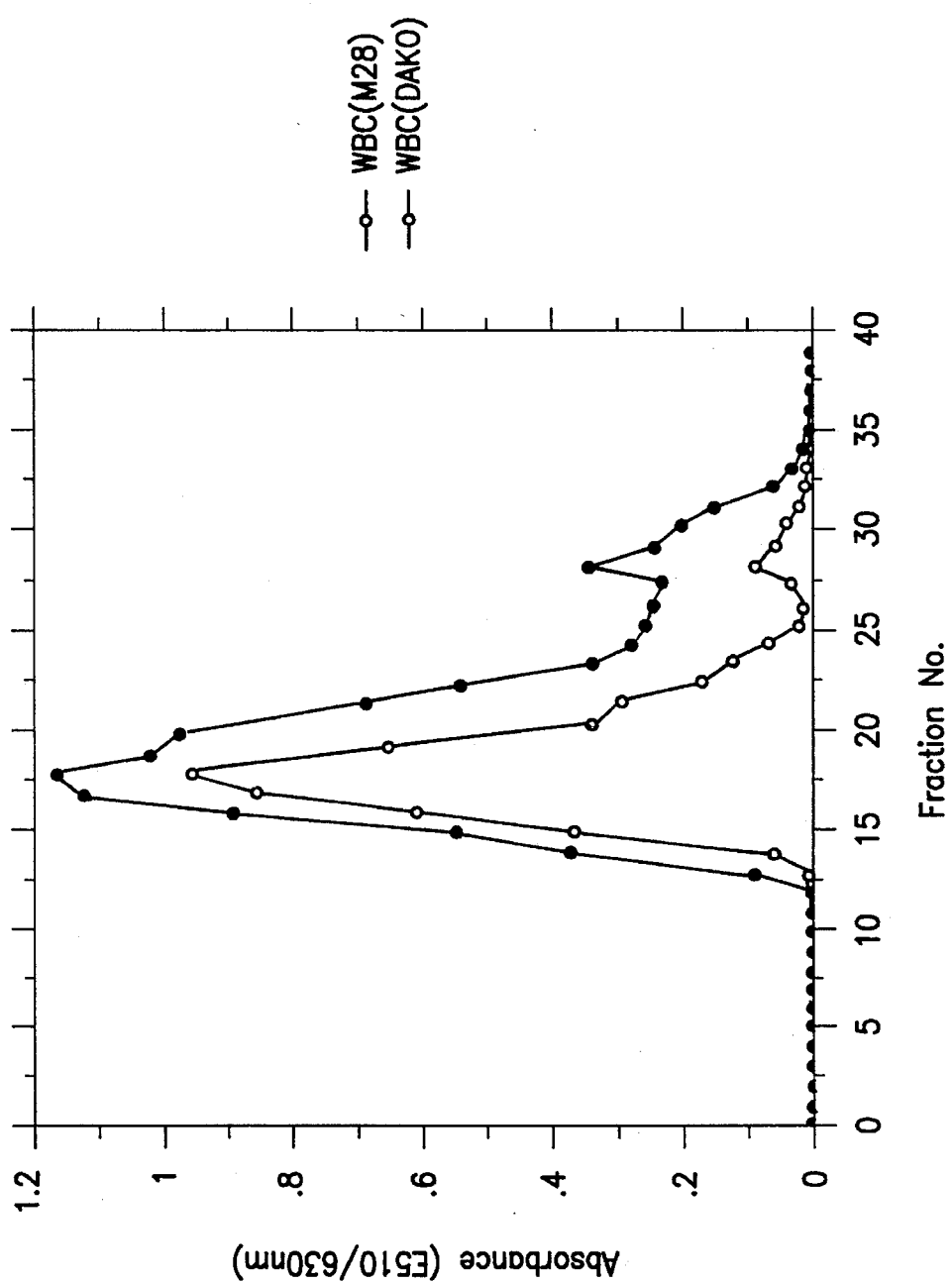
FIG. 18 shows reactivities of polyclonal antibody (DAKO) and monoclonal antibody M28 with lactoferrin derived from neutrophilic leukocytes by gel filtration chromatography and ELISA.
Figure 20:
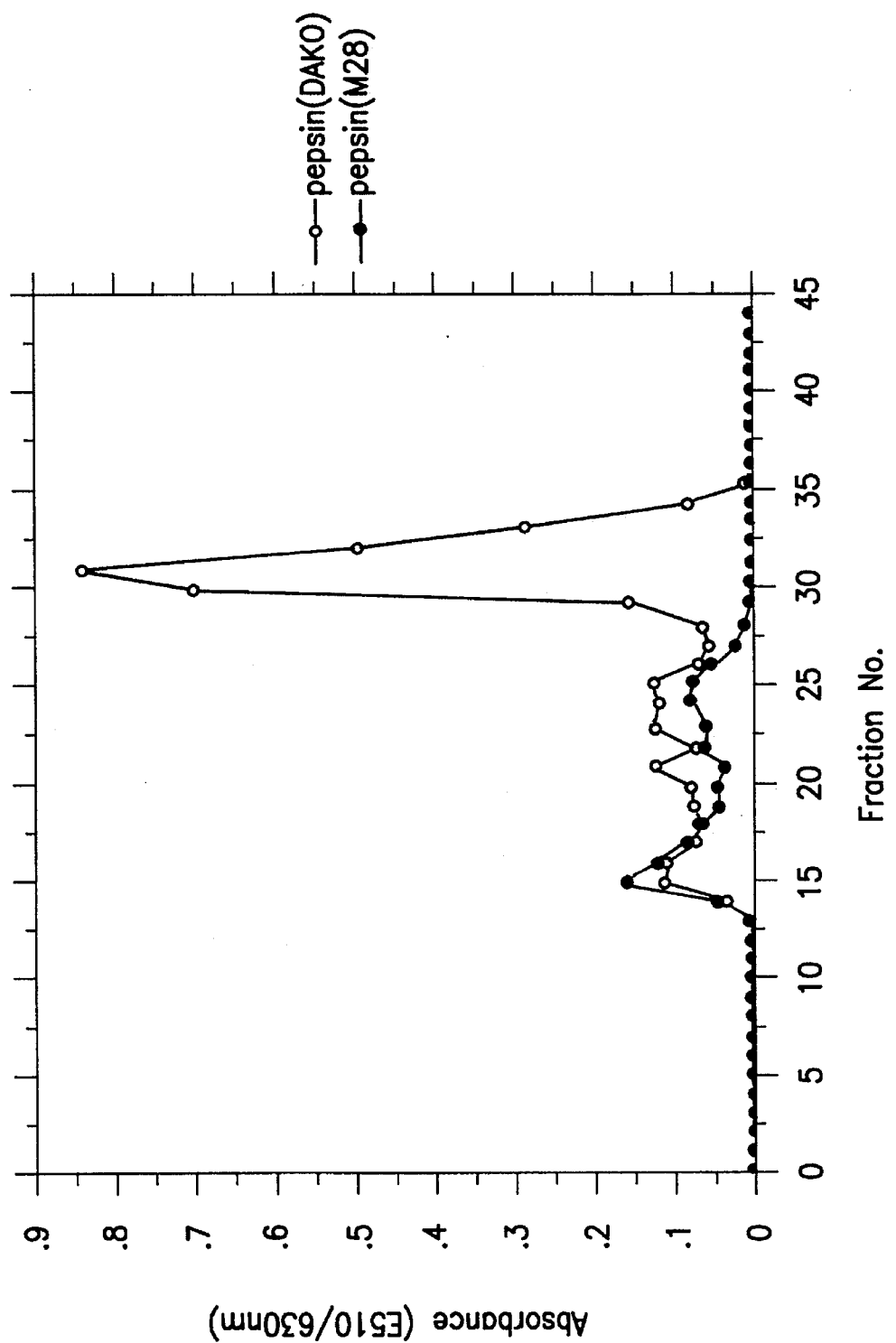
FIG. 20 shows reactivities of polyclonal antibody (DAKO) and monoclonal antibody M28 with half-sized lactoferrin obtained after treating with pepsin in a fecal sample by gel filtration chromatography and ELISA.
Figure 21:
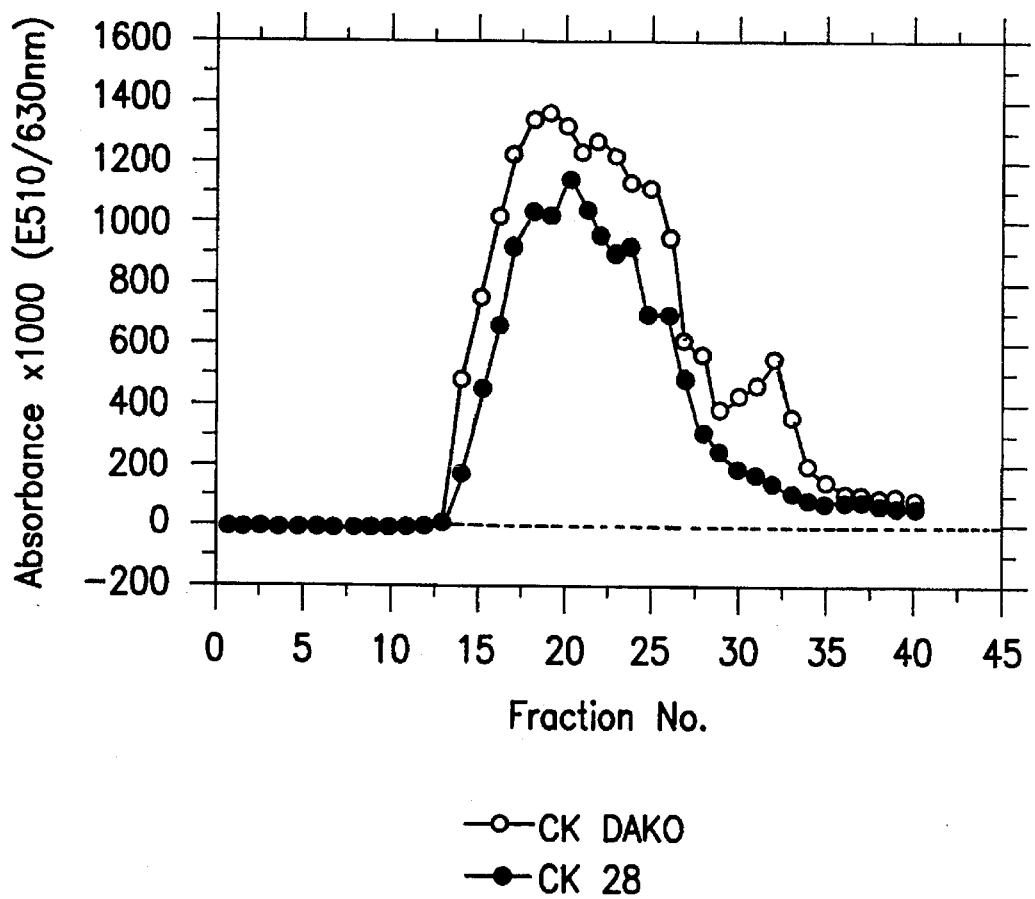
FIG. 21 shows reactivity of polyclonal antibody (DAKO) and monoclonal antibody M28 with lactoferrin in a fecal sample by gel filtration chromatography and ELISA.
Figure 22A:
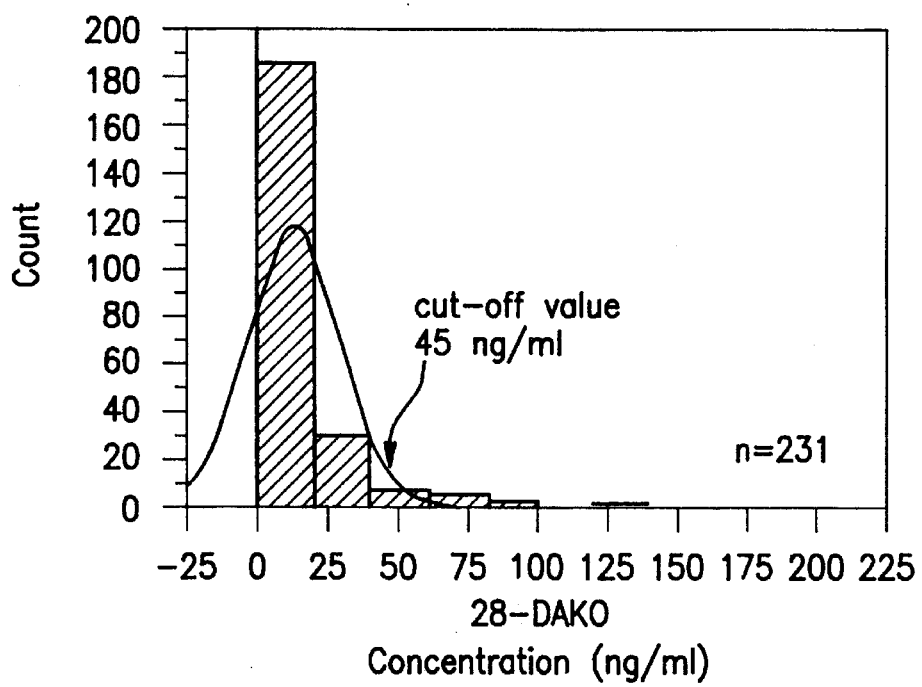
FIGS. 22A and 22B show cut-off values of lactoferrin in fecal samples from healthy persons obtained by ELISA using polyclonal antibody (DAKO) and monoclonal antibody M28.
Figure 22B:
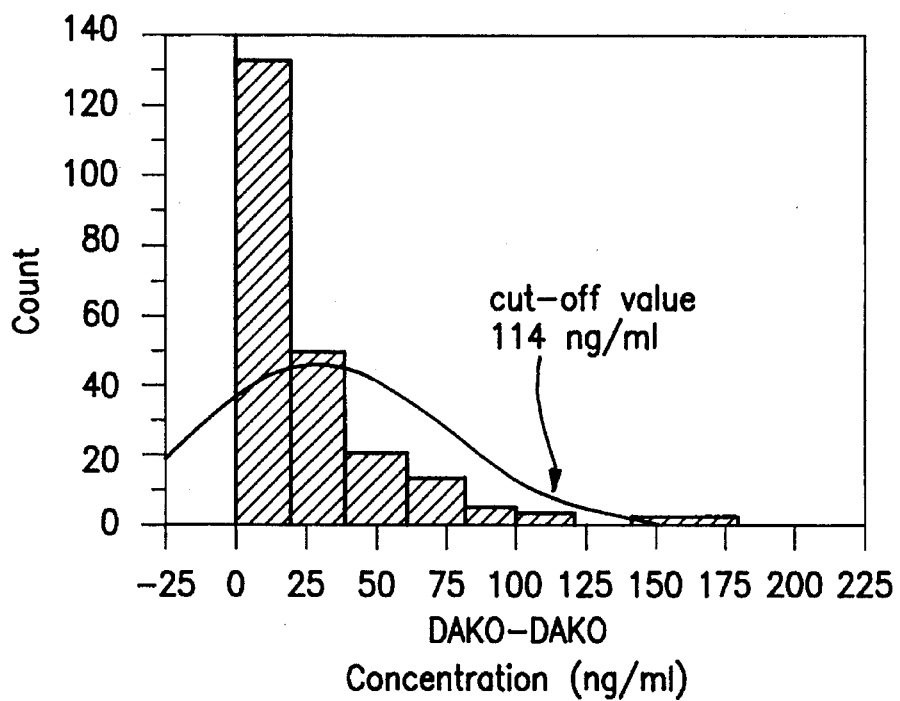
Figure 23:
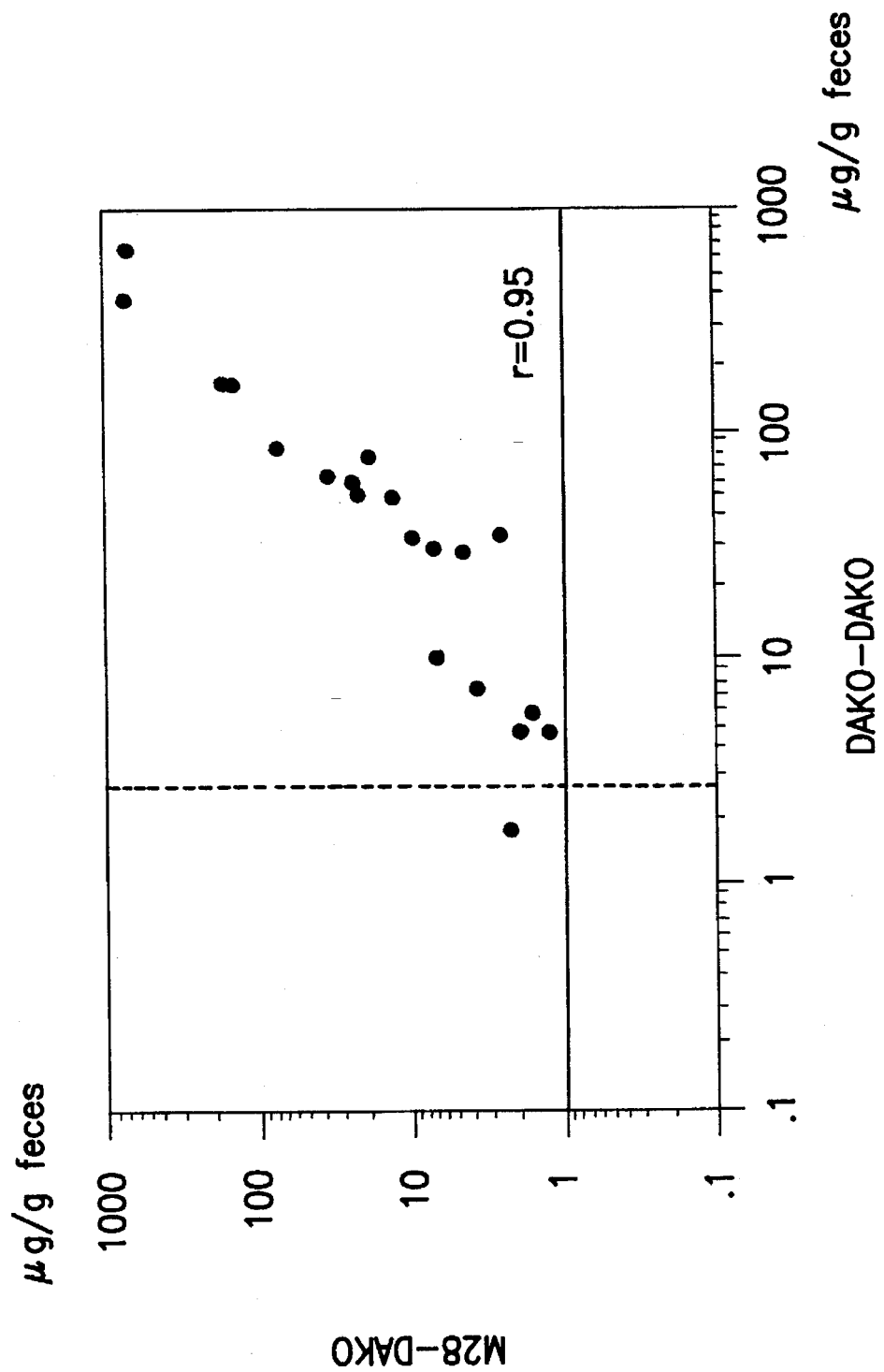
FIG. 23 shows lactoferrin concentrations in fecal samples from patients with colorectal cancer by ELISA using polyclonal antibody (DAKO) and monoclonal antibody M28.

The hemoglobin concentrations in each group were: 1.9±2.0 μg/g feces in the control group, 33.1±68.8 in the colon polyp group, 1162.8±1705.2 in the colorectal cancer group, 2939.5±3435.5 in the active ulcerative colitis group, 117.5±481.8 in the inactive ulcerative colitis group, 175.0±363.3 in the active Crohn's disease group, and 39.2±120.9 in the inactive Crohn's group (FIG. 10).

Example 6

Mass screening of colorectal cancer

Mass screening of colorectal cancer using lactoferrin assay of the invention and occult blood immunochemical test (referred to as occult blood test, hereinafter) were carried on 2300' subjects.

The positive rates are 4.2% in lactoferrin assay and 5.4% in occult blood test. The positive rate is 50/2300 (2.2%) in both lactoferrin assay and occult blood test, and those are 47/2300 (2.0%) in only lactoferrin assay and 75/2300 (3.2%) in only occult blood test, respectively. The results show that there were many subjects who were judged as positive by occult blood test and were not judged as negative by lactoferrin assay, and that a false positive ratio is lower in lactoferrin assay than that in occult blood test.

Example 7

One hundred μl of 0.1 mol/l Tris-buffer (pH 8.0) containing 5 μg/ml of anti-human-lactoferrin antibody (Monoclonal antibody M28) was placed in each well of a 96-well polystyrene microplate (SUMILON, Japan) and left overnight at 4° C., so that the monoclonal M28 was physically adsorbed on each surface of the wells. On the other hand, anti-human-lactoferrin antibody (DAKOPATT, Denmark) was labeled with alkaline phosphatase (Boehringer Mannheim, F.R.G.) by the periodic acid Schiff stain method. Then, Tris buffer (0.1 mol/l pH 8.0) containing 100 μl of 1% BSA (Boehringer Mannheim, F.R.G.) was separately injected into each well of the microplate, to which 50 μl of fecal specimen was added. The mixture was stirred and allowed to stand at 37° C. for one hour and then washed three times with deionized water containing 0.05% of Tween-20. Then 100 μl of alkaline phosphatase-labeled anti-human-lactoferrin antibody solution containing 1% of BSA Tris-saline buffer was added to each well, allowed to react at 37° C. for another hour and washed three times.

A substrate buffer (disodium phenylphosphate: 0.215 g (WAKO Junyaku, Japan) and 4-aminoantipyrine: 0.09 g (WAKO Junyaku, Japan) were dissolved in 100 ml of carbonate buffer solution (0.05M, pH: 10.15)) according to the Kind-King method, 100 μl was added into each well and allowed to react at 37° C. for 30 minutes. Then 100 μl of coloring reagent (a mixture of 2.6g boric acid (WAKO Junyaku, Japan) dissolved in 200 ml of deionized water and 0.38 g potassium ferricyanide (WAKO Junyaku, Japan)) was added to each well to produce a color reaction. The color of each well was assessed by determining absorbance at 510/630 nm with a microplate photometer (Sanko Junyaku, Japan). Lactoferrin concentration in the fecal specimens was obtained from a lactoferrin quantification curve.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A screening test method for colorectal cancer carried out on a fecal sample of a person suspected of suffering from colorectal cancer which comprises determining the amount of lactoferrin in the fecal sample by immunoassay, wherein an amount of more than 2.4 μg lactoferrin per g feces indicates colorectal cancer.

2. A screening test method for colorectal cancer carried out on a fecal sample of a person suspected of suffering from colorectal cancer which comprises determining the amount of myeloperoxidase in the fecal sample by immunoassay, wherein an amount of more than 4.2 μg myeloperoxidase per g feces indicates colorectal cancer.

3. The screening test method according to claim 1, in which the determination is made by contacting the fecal sample with anti-human-lactoferrin antibody.

4. The screening test method according to claim 2, in which the determination is made by contacting the fecal sample with anti-human-myeloperoxidase antibody.

5. The screening test method according to claim 3, in which the determination is made by contacting the fecal sample with anti-human-lactoferrin antibody in an enzyme-linked immunosorbent assay.

6. The screening test method according to claim 4, in which the determination is made by contacting the fecal sample with anti-human-myeloperoxidase antibody in an enzyme-linked immunosorbent assay.

7. A screening test method for colorectal cancer carried out on a fecal sample of a person suspected of suffering from colorectal cancer which comprises determining the amount of whole-sized human lactoferrin (µg/g) in the fecal sample by immunoassay utilizing monoclonal antibody to whole-sized human lactoferrin.

8. A screening test method for colorectal cancer carried out on a fecal sample of a person suspected of suffering from colorectal cancer which comprises determining the amount of whole-sized human lactoferrin in the fecal sample by immunoassay utilizing monoclonal antibody to whole-sized human lactoferrin, wherein an amount of more than 1.0 µg whole-sized lactoferrin per g feces indicates colorectal cancer.

9. The screening test method according to claim 7 or claim 8 in which said monoclonal antibody neither reacts with lactoferrin previously exposed to acidity of about pH 2, nor with lactoferrin previously treated with pepsin.

* * * * *